US00RE45186E

(19) United States
(12) Reissued Patent
Shen et al.

(10) Patent Number: US RE45,186 E
(45) Date of Reissued Patent: Oct. 14, 2014

(54) LOW COST ROOM TEMPERATURE ELECTROCHEMICAL CARBON MONOXIDE AND TOXIC GAS SENSOR WITH HUMIDITY COMPENSATION BASED ON PROTONIC CONDUCTIVE MEMBRANES

(75) Inventors: Yousheng Shen, Draper, UT (US); Franco Consadori, San Juan Capistrano, CA (US); D. George Field, Pleasant Grove, UT (US)

(73) Assignee: Atwood Mobile Products Inc., Elkhart, IN (US)

(21) Appl. No.: 10/621,637

(22) Filed: Jul. 17, 2003

Related U.S. Patent Documents

Reissue of:

(64) Patent No.: 5,650,054
Issued: Jul. 22, 1997
Appl. No.: 08/522,946
Filed: Sep. 1, 1995

U.S. Applications:

(63) Continuation-in-part of application No. 08/381,718, filed on Jan. 31, 1995, now Pat. No. 5,573,648.

(51) Int. Cl.
*G01N 27/407* (2006.01)

(52) U.S. Cl.
USPC ..... 204/412; 204/421; 204/424; 205/781; 205/783.5; 205/784; 205/786.5; 205/788

(58) Field of Classification Search
USPC ..... 204/412, 421–429; 205/781, 783.5, 205/784, 786.5, 788
See application file for complete search history.

(56) References Cited

U.S. PATENT DOCUMENTS 3,366,559 A * 1/1968 Leisle et al. ..... 205/152
4,024,036 A * 5/1977 Nakamura et al. ..... 204/266

(Continued)

FOREIGN PATENT DOCUMENTS

EP 637 851 A1 6/1994

OTHER PUBLICATIONS

Mahlon S. Wilson, Fernando H. Garzon, Kurt E. Sickafus, and Shimshon Gottesfeld, Surface Area Loss of Supported Platinum in Polymer Electrolyte Fuel Cells, vol. 140, No. 10, Oct. 1993.*

(Continued)

*Primary Examiner* — Kaj K Olsen
(74) *Attorney, Agent, or Firm* — Banner & Witcoff, Ltd.

(57) ABSTRACT

A low cost room temperature electrochemical gas sensor with humidity compensation for sensing CO, alcohol vapors and other toxic analyte gases has a solid protonic conductive membrane with a low bulk ionic resistance. A sensing electrode and a counter electrode, optionally a counter electrode and a reference electrode, which are separated by the membrane, can be made of mixed protonic-electronic conductors, or can be made of a thin electrically conducting film such as platinum. A reservoir of water maintain the solid protonic conductive membrane at constant 100 percent relative humidity to compensate for ambient humidity changes. Embodiments of the inventive sensor also include an electrochemical analyte gas pump to transport the analyte gas away from the counter electrode side of the sensor. Analyte gas pumps for the inventive sensor include dual pumping electrodes situated on opposite sides of the membrane, and include a means for applying a DC power across the membrane to the sensing and counter electrodes. Another embodiment of the inventive sensor has first and second solid protonic conductive membranes, one of which has a sensing electrode and a counter electrode separated by the first membrane, and the other of which has dual pump electrodes situated on opposite sides of the second membrane.

130 Claims, 6 Drawing Sheets

(56) References Cited

U.S. PATENT DOCUMENTS

| | | | | | |
|---|---|---|---|---|---|
| 4,025,412 | A | * | 5/1977 | LaConti | 204/424 |
| 4,227,984 | A | * | 10/1980 | Dempsey et al. | 204/408 |
| 4,324,632 | A | * | 4/1982 | Tantram et al. | 204/415 |
| 4,474,648 | A | * | 10/1984 | Tantram et al. | 205/783 |
| 4,478,704 | A | * | 10/1984 | Miyoshi et al. | 204/412 |
| 4,536,274 | A | * | 8/1985 | Papadakis et al. | 204/433 |
| 4,664,757 | A | * | 5/1987 | Zupancic et al. | 205/783 |
| 4,804,592 | A | * | 2/1989 | Vanderborgh et al. | 429/33 |
| 4,820,386 | A | * | 4/1989 | LaConti et al. | 205/779.5 |
| 4,913,792 | A | * | 4/1990 | Nagata et al. | 204/412 |
| 5,080,775 | A | * | 1/1992 | Yamauchi et al. | 204/424 |
| 5,118,398 | A | * | 6/1992 | McElroy et al. | 205/775 |
| 5,126,035 | A | * | 6/1992 | Kiesele et al. | 204/415 |
| 5,133,857 | A | * | 7/1992 | Alberti et al. | 204/425 |
| 5,164,053 | A | * | 11/1992 | Razaq et al. | 205/784 |
| 5,173,166 | A | * | 12/1992 | Tomantschger et al. | 204/412 |
| 5,228,974 | A | * | 7/1993 | Kiesele et al. | 204/415 |
| 5,302,274 | A | * | 4/1994 | Tomantschger et al. | 204/412 |
| 5,322,602 | A | * | 6/1994 | Razaq | 205/788 |
| 5,330,860 | A | * | 7/1994 | Grot et al. | 429/42 |
| 5,344,546 | A | * | 9/1994 | Kiesele et al. | 204/415 |
| 5,403,452 | A | * | 4/1995 | Hielscher et al. | 205/781 |
| 5,474,857 | A | * | 12/1995 | Uchida et al. | 429/33 |
| 5,635,039 | A | * | 6/1997 | Cisar et al. | 204/252 |

OTHER PUBLICATIONS

"Humidity Dependence of Carbon Monoxide Oxidation Rate in a Nafion-Based Electrochemical Cell," Lee et al., Technical Papers, Solid-State Science and Technology, J. Electrochem. Soc., vol. 142, No. 1, Jan. 1995; pp. 157-160.

"Recent Developments in Electrochemical Solid Polymer Electrolyte Sensor Cells for Measuring Carbon Monoxide and Oxides of Nitrogen," La Conti et al., Chemical Hazards in the Workplace: Measurement and Control, ACS Symposium, series 149, 1981; pp. 551-573.

"Effects of Surface Roughening of Nafion$^r$ on Electrode Plating, Mechanical Strength, and Cell Performances for SPE Water Electrolysis," Sakai et al., J. Electrochem. Soc., 137:3777-3783, 1990.

"Chemical Sensing with Solid State Devices," Madou and Morrison, Academic Press, Inc., pp. 448-459, 1989.

"Fuel Cell Systems," Edited by Blomen and Mugerwa, Plenum Press, Srinivasan et al., pp. 48-52 and 63-67, 1993.

Notice of Opposition in European Patent No. 762117B, including Opponent's statement of grounds (entitled "Reasons") (18 pages total).

Sung B. Lee, Anthony Cocco, Darioush Keyvani and G. Jordan Maclay, *Humidity Dependence of Carbon Monoxide Oxidation Rate in a Nafion-Based Electrochemical Cell,* vol. 142, No. 1, Jan. 1995.

* cited by examiner

LOW COST ROOM TEMPERATURE ELECTROCHEMICAL CARBON MONOXIDE AND TOXIC GAS SENSOR WITH HUMIDITY COMPENSATION BASED ON PROTONIC CONDUCTIVE MEMBRANES

Matter enclosed in heavy brackets [ ] appears in the original patent but forms no part of this reissue specification; matter printed in italics indicates the additions made by reissue.

This is a continuation-in-part of U.S. Pat. application Ser. No. 08/381,718 Filed on Jan. 31, 1995, now U.S. Pat. No. 5,573,648, titled "Gas Sensor Based on Protonic Conductive Membranes", which is incorporated herein by reference.

1. The Field of the Invention

The invention relates to electrochemical gas sensors, and particularly relates to humidity compensated electrochemical gas sensors having a sensing electrode, a counter electrode, and a solid proton conductor for room temperature detection of the concentration of carbon monoxide (CO) in the ambient.

2. Background of the Invention

In most prior art solid state commercial gas sensors, it is necessary to heat the sensor element to elevated temperatures in order to acquire both fast response time and high sensitivity to objective gases. For example, N-type semiconductor tin oxide gas sensors and catalytic combustion type Pd/Pt gas sensors must usually be operated in a temperature range of ca. 200° to 500° C. These sensors must be equipped with heaters connected to external power sources. Therefore, room temperature CO gas sensors, which use less power, are desirable.

It is well known that CO reacts with moisture in air at room temperature, and forms protons, electrons, and $CO_2$ in an oxidation reaction of CO.

$$CO+H_2O \rightarrow CO_2+2H^++2e^- \quad (1)$$

It is also known that there is a moisture formation reaction by combining protons, electrons, and oxygen in a reduction reaction of oxygen:

$$2H^++2e^-+2O_2 \rightarrow H_2O \quad (2)$$

These two reactions are the basis of prior art room temperature zero power electrochemical gas sensors utilizing a proton conductor. FIG. 1 shows the transport processes of such a CO gas sensor. A protonic conductor 12 conducts ionized hydrogen atoms from a sensing electrode 16 where the sensor signal originates from the oxidation reaction of carbon monoxide at sensing electrode 16. Ionized hydrogen atoms, each of which constitutes a single proton, are conducted through protonic conductor 12 to a counter electrode 14. Electrons that are liberated in the oxidation of carbon monoxide at sensing electrode 16 are conducted through an electrical lead 22 to voltage meter 18, through an electrical lead 20, and to counter electrode 14 for a reduction reaction of oxygen. In a steady state reaction, the hydrogen ions are transported from sensing electrode 16 to counter electrode 14 in the depicted potentiometric CO gas sensor.

The current generated by the reactions depicted in FIG. 1 can also be measured by an amp meter 24 having a resistor $R_L$ 26, which circuit represents a transport process of an amperometric CO sensor. Absent amp meter 24, resistor $R_L$ 26, the leads thereto which are shown in phantom, transport processes of a potentiometric CO gas sensor are shown for voltage meter 18 and leads 20, 22.

Whether the transport processes shown in FIG. 1 are for potentiometric CO gas sensor or for an amperometric CO sensor, electrons from the process of the oxidation reaction of carbon monoxide travel as seen in arrow 21 in FIG. 1 through leads 20, 22.

The sensor of FIG. 1 is operated in a current mode when the sensing and counter electrodes 16, 14 are connected to each other through load resistor $R_L$, or are connected to a DC power source (not shown) which electrically drives the protons across proton conductor 12.

A prior art room temperature proton conductor sensor developed by General Electric using a polymer porous support material saturated by a liquid proton conductor, has been constructed as an electrochemical amperometric CO gas sensor (the G. E. Sensor). In the G. E Sensor, a liquid reservoir was used to provide the liquid proton conductor to the porous support material. Protons, which are indicative of the ambient CO concentration, were driven across the porous support material through the liquid conductor by a DC voltage. Electrical current response of the sensor to ambient CO concentration was linear. The cost of the sensor with such a complicated design, however, is high and is thus not be suitable for practical consumer applications.

In U.S. Pat. No. 4,587,003, a room temperature CO gas sensor using a liquid proton conductor is taught. Basically, the mechanism and design of the sensor were similar to the G. E. sensor, except that the outside surfaces of the sensing and counter electrodes of the sensor in this patent were coated by porous NAFION™ layers. The CO room temperature gas sensor taught in the patent currently costs about $200.00. The lifetime of such a sensor is about 6-12 months due to the rapid drying of the liquid of the electrolytes. In addition, the sensor requires maintenance due to leakage and corrosion of liquid electrolyte.

Other types of gas sensors incorporating a liquid proton conductive electrolyte are also known. In particular, U.S. Pat. No. 5,228,974 discloses a liquid proton conductive electrolyte of an aqueous solution of calcium nitrate and lithium nitrate. Additionally, U.S. Pat. No. 5,126,035 discloses another liquid proton conductive electrolyte.

It is necessary in prior art gas sensors to routinely re-calibrate the gas sensor so that the drift of its output signal can be corrected. This drift in the signal is due to the fact that such sensors must be exposed to the ambient in order to sample the desired target gases and, through such exposure, the liquid electrolyte slowly dries during the sensor service time, as described above. As a result of this process, the proton conductivity of the liquid electrolyte changes and the change in relationship between electrical current and gas concentration results in the need to re-calibrate these gas sensors. The re-calibration requirement of such gas sensors limits their applications. For instance, it would be impractical to install a carbon monoxide sensor in a residential home that required re-calibration. As such, re-calibratable gas sensors may be suitable for industrial lab applications and would be practically excluded from consumer applications.

Liquid proton conductive electrolytes used in current amperometric room temperature electrochemical gas sensors are known to have long term stability problem. One such source of problems threatening stability of such sensors is the use of fine noble metal particles in such gas sensors to catalyze the electrochemical reactions with the target gas.

It is known that an electrical or an electrochemical driving force such as DC power for a period of time, such as a month or longer, will cause the size of the noble metal particles used in such centers to increase. Particle size increase will cause a reduction in performance of the sensor so as to affect its long term sense of stability in accurate sensor signal output. Additionally, in prior art gas sensors a large gap is needed between the sensing electrode and the counter electrode to ensure that a liquid electrolyte can mix and maintain a uniform distribution in prior art gas sensors. As a consequence of the large gap between electrodes, the internal conductivity of the sensor becomes too small to generate a detectable current signal therebetween. As such, a DC power source is required to act upon the gas sensor as a driving force so as to generate a detectable proton current. Additionally, while DC power is being supplied to the gas sensor, water moisture or vapor in the ambient decomposes into protons, electrons, and oxygen.

The background proton electrical current is a function of both humidity and voltage of the DC power source. Should there be a change in either humidity or DC bias voltage, then the background proton electrical current also changes with the resulting error in the signal output from the sensor. Thus, gas measurements using such prior art gas sensors are inaccurate.

From the above, it can be seen that there is a need for a practical, electrochemical, room temperature gas sensor that does not require periodic re-calibration, that does not experience background electrical current drift, and does not experience long term stability problems.

The discovery of room temperature solid proton conductors aroused considerable efforts to investigate low cost, all-solid electrochemical room temperature CO gas sensors. One such sensor that was developed was a room temperature CO gas sensor with a tubular design using proton conductors, electronically conductive platinum or the like as the sensing electrode, and electronically conductive silver, gold, graphite or the like as the counter electrode. The sensing electrode decomposed carbon monoxide gas to produce protons and electrons, whereas the counter-reference electrode exhibited no activity to decompose carbon monoxide with the result that a Nernst potential occurred between the two electrodes. Thus, carbon monoxide gas was detected.

In detecting carbon monoxide with the tubular design sensor, protons and electrons are generated at the sensing electrode. For the reaction to be continued, protons and electrons must be removed from the reaction sites, and CO and moisture must be continuously provided from the gaseous phase to the reaction sites. Therefore, the CO reaction only occurs at three-phase contact areas. The three-phase contact areas consist of the proton membrane phase, the platinum electron phase, and the gas phase. Due to the limited three-phase contact areas in the tubular design sensor, the CO reaction was slow. Additionally, as a result of this slow reaction, the response signal was weak. Further, the Nernst potential was not zero in clean air.

A modified electrochemical CO room temperature gas sensor using a planar or tubular sensor design was a subsequent development to the earlier tubular design CO sensor. In order to overcome the problem that the Nernst potential is not zero in clean air experienced with the earlier tubular design CO sensor, the improved design proposed a four probe measurement method for CO gas detection. The improved design achieved a zero reading in clean air, and the improved sensor was insensitive to variations in relative humidity. Theoretical analysis based on electrochemistry, however, indicates that there is no difference between the four probe method and the normal two probe method of the earlier tubular design CO sensor. The improved sensor still used electronic conductors for both the sensing and counter electrodes, and showed slow and weak response signals to CO gas.

A still further improved design of a CO sensor is a room temperature electrochemical gas sensor using a solid polymer proton conductor with a planar sensor design. Response of this further improved sensor to CO was very weak, and was in the nA range even as a DC power source was applied. Apparently, the internal resistance of the sensor was too large. Calculations based on this further improved sensor dimensions indicates that the ionic resistance of the proton conductor membrane is about 400 K-ohm, which is too large to generate a useable strong signal. Further development and improvement of the planar CO gas sensor, which incorporated a sensing mechanism, resulted in performance that was still in nA range of sensor response.

From the above, it can be seen that it would be desirable to provide a solid proton conductor in a gas sensor that had a strong response signal and was relatively rapid in response. Additionally, it would be desirable to provide humidity compensation with both a strong and rapid signal response from the gas sensor.

SUMMARY AND OBJECTS OF THE INVENTION

It is an object of this invention to provide a low cost room temperature, electrochemical gas sensor, for carbon monoxide and other toxic gases, having a low ionic resistance, a rapid response, and a strong signal to the detection of gaseous CO in the ambient. The alcohol and toxic gases that can be sensed by the inventive sensor, each of which is referred to herein as an analyte gas, include methyl alcohol, ethyl alcohol, etc, and may also include $H_2$, $H_2S$, $H_2O$ vapor, Nox, etc.

It is a further object of the present invention to provide an electrochemical, room temperature gas sensor that does not require periodic re-calibration, that eliminates background electrical current drift, and that does not experience long term instability problems known to prior art gas sensors.

It is a further object of this invention to provide a solid proton conductive thin membrane electrolyte, the conductivity of which is time independent, and has a large enough conductivity so that no DC power is needed to drive the electrical proton current.

The inventive electrochemical sensor has both a sensing electrode and a counter electrode, or optionally a sensing electrode, a count electrode, and a reference electorode. Each of the sensing and counter electrodes can be made of a thin layer of a noble metal or, alternatively, a thicker layer of mixed protonic-electronic conductors so as to encourage a high surface area for reactions at the electrodes, either of which cause fast analyte gas reaction kinetics and a continuity in the transport of electrical charges so as to avoid polarization effects at the electrodes, thus achieving a fast and strong signal response by the sensor in the presence of the analyte gas.

A further aspect of the inventive gas sensor is that either two electrodes or three electrodes are required, whereas prior art gas sensors always require three electrodes and a DC power supply.

These objects have been achieved by an electrochemical room temperature gas sensor having a solid proton conductive electrolyte membrane. The gas sensor has a lower cap having a water reservoir therein, a perforated washer covered over by a hydrophobic microporous lower membrane, a proton conductive membrane coating with catalysts on both sides serving as electrodes thereto, a sealing ring that electrically insulates the lower cap containing the water from a perforated upper cap. Optionally, the gas sensor may be also provided with a dust filter covering over the perforations to the upper cap to prevent the contamination of the inside of the gas sensor from ambient dust. The novel sensor design, may include thin film noble metal or mixed proton-electron conductive electrodes, various embodiments of which may also include an electrochemical analyte gas pump to transport analyte gas away from the counter electrode side of the gas sensor. While the inventive sensor is referred to herein as a CO sensor, it is contemplated that the inventive sensor is also capable of sensing alcohol gases and other toxic analyte gases disclosed herein.

These and other objects and features of the present invention will become more fully apparent from the following description and appended claims, or may be learned by the practice of the invention as set forth hereinafter.

BRIEF DESCRIPTION OF THE DRAWINGS

In order that the manner in which the above-recited and other advantages and objects of the invention are obtained, a more particular description of the invention briefly described above will be rendered by reference to specific embodiments thereof which are illustrated in the appended drawings. Understanding that these drawings depict only a typical embodiment of the invention and are not therefore to be considered to be limiting of its scope, the invention will be described and explained with additional specificity and detail through the use of the accompanying drawings in which.

DETAILED DESCRIPTION OF THE PREFERRED EMBODIMENTS

Figure 1:
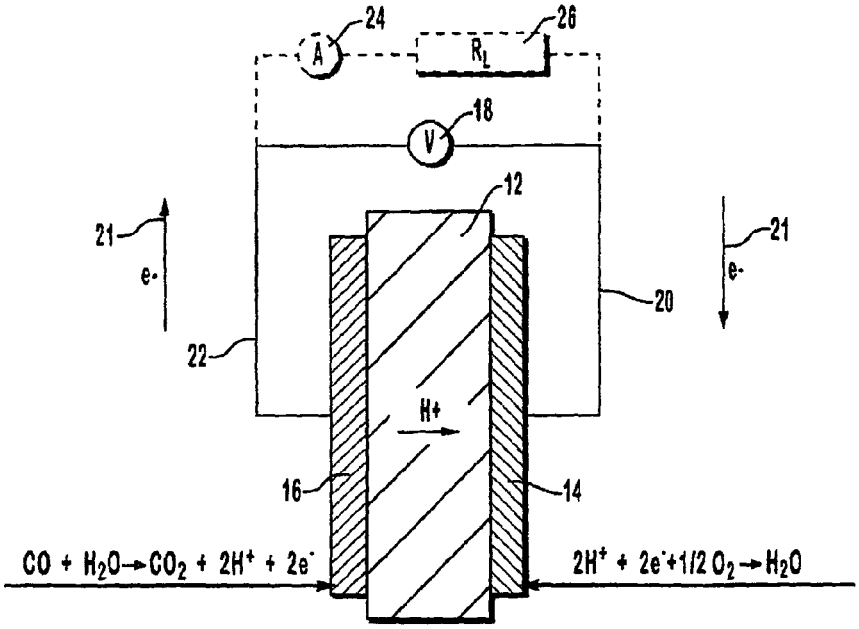
FIG. 1 is an electrochemical gas sensor showing the transport processes of both a potentiometric CO sensor and an amperometric CO sensor, where hydrogen protons are conducted through a protonic conductive membrane situated between sensing and counter electrodes, where electrons travel between said electrodes away from the protonic conductive membrane, where the sensing electrode is the locus of the oxidation reaction of carbon monoxide instigated by a catalyst, and the counter electrode is the locus of the synthesis of water from the products of the electrochemical reaction of the sensor.

The inventive CO sensor features a solid protonic conductive membrane operable at room temperature and having a fast and high signal response. To achieve a fast detection time and a high signal response, it is desirable to provide a CO sensor having a low bulk ionic resistance. Bulk ionic resistance $R_{bulk}$ of the inventive sensor is equal to $$R_{bulk} = R_o \frac{d}{S} \tag{3}$$

where $R_o$ is the ionic specific resistivity of the protonic conductive membrane, S is the cross section area of the protonic conductive membrane between the two electrodes, and d is the thickness of the protonic conductive membrane.

Resistance of an electrochemical cell includes at least three components: 1) bulk ionic resistance of the membrane, 2) interface resistance between the membrane and electrodes, and 3) electronic resistance of the electrodes. The bulk ionic resistance of the sensor is reduced to about 1 ohm by the inventive sensor design, such that $R_{bulk}$ is not a performance limit. Electronic resistivity of the electrodes is in order of $10^5$ ohm-cm and is not a performance limit. Therefore, the interface resistance, which is relative to the available three-phase contact area, becomes the performance limit. The interface resistance of the sensor according to this invention has been reduced by introducing mixed proton-electronic conductor, or alternatively, a thin film electron conductor electrode.

Reference is now made to FIGS. 1-8 wherein like reference numerals between different embodiments of the inventive sensor designate like features.

In FIG. 1, electrical leads 22, 20 are in electrical communication, respectively, with sensing electrode 16 and counter electrode 14. Measurement of signals output by the sensor seen in FIG. 1 is seen in two alternative embodiments. In a first embodiment, a voltage meter 18 measures potential differences between electrical leads 20, 22 in a potentiometric CO gas sensor embodiment. In a second embodiment, an amp meter 24, in combination with a resistor $R_L$ 26 provides an amperometric CO sensor embodiment. Electrical circuitry, as seen in FIG. 1, can be used in other CO sensor embodiments depicted and described elsewhere to measure the output thereof. Additionally, such electrical circuity serves as an example and illustration of a means for electrical measurement that is electrically connected to the sensing and counter-reference electrodes.

Figure 2:
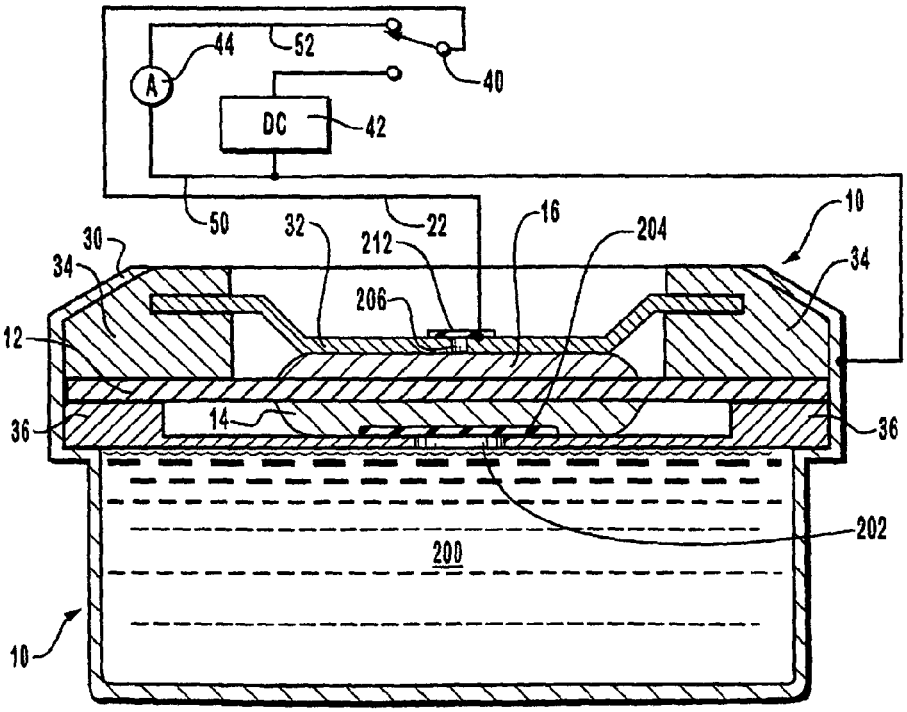
FIG. 2 shows an embodiment for the inventive electrochemical gas sensor that is contained in a water containing can having a cap which encloses a counter electrode and a sensing electrode, where a protonic conductor is situated between the electrodes, which electrodes are separated by insulated packing material within the can and cap container arrangement.

A sensor 10 in FIG. 2 is shown with an electrically conductive can 30 having a reservoir 200 filled with de-ionized water. Can 30 is an example and illustration of a means, containing a volume of water vapor, for exposing a surface of a counter electrode to the water vapor. Upon such exposure to an atmospheric concentration of a target gas, such as CO, electrical measurements can be made to detect changes in electrical characteristics of the electrodes.

The de-ionized water in can 30 may contain an antifreeze additive, such as glycol or other known antifreeze. Can 30 may have a sealable opening therein to replenish water in reservoir 200. Reservoir 200 is separated from counter electrode 14 by a large hole 202 in an electrically conductive washer 36 covered over by a microporous hydrophobic filter 204. Can 30 has an opening which is covered by a metallic cap 32. Cap 32 has a small air sampling hole 206 therein so as to provide a venting of sensing electrode 16 to the ambient. Hole 206 is optionally covered over with a dust filter 212 to prevent contamination of sensing electrode 16 by ambient dust and other air borne particulate matter. An insulation packing material 34 electrically insulates cap 32 from can 30. Cap 32, can 30, and washer 36 need not be electrically conductive when electrical leads 50, 22 are embedded, respectively, within electrodes 14, 16.

In FIG. 2, electrical leads 50, 22 are connected to a switching mechanism for sensor 10 made up of a switch 40 that is opened and closed by unit 42 so as to alternatively provide a power source 44 in electrical communication with cap 32 and can 30 of sensor 10. Unit 42, and related circuitry, serves as an example and illustration of a means for applying a DC power across the protonic conductive electrolyte membrane, and switch 40 and related circuitry serves as an example and illustration of a switch means for alternating the connection between the sensing and counter electrodes from the electrical measurement means to the DC pulse power means.

The purpose of the foregoing electrical switching circuitry is to provide a switchable CO pump to sensor 10 so as to direct CO away from counter electrode 14 before and after sensing and measuring CO concentration with sensor 10. If switchable CO pump circuitry is not included in the embodiment of sensor 10 shown in FIG. 2, then continuous sensing without CO pumping is performed by sensor 10.

The amperometric sensor also can be combined with an electrochemical CO pump, as defined hereinafter, and an accurate response will be achieved in such combined sensors.

The presence of the water vapor from the de-ionized water in reservoir 200 assures a 100% relative humidity exposure to the sensing electrode, protonic conductor and the sensing electrode, protonic conductor, and the counter electrode at all times. This is particularly important in that the resistance of the solid proton conductive electrolyte membrane is a function of the water vapor pressure to which the electrolyte membrane is exposed. As such, the proton conductivity of the electrolyte membrane is constant throughout the sensor's life and does not require re-calibration, where such life is dependent upon the presence of water in reservoir 200.

Hole 202 in washer 36 is preferably larger than hole 206 in cap 32. Preferably, hole 202 will have a diameter of approximately 3 mm and hole 206 will have a diameter of approximately 0.2 mm. The relative diametric differences between holes 202, 206 ensure that water vapor pressure at protonic conductive membrane 12, sensing electrode and counter electrode will be sufficient to saturate the same and be constant as long as reservoir 200 contains water therein. Over a period of the useful service life of sensor 10, the water and reservoir 200 will be evaporated. The proton conductivity of protonic conductive membrane 12, however, will remain constant and sensor 10 will not require re-calibration while water is present.

While FIG. 2 is depicted with a DC power source, it should be understood that the embodiment shown in FIG. 2 of the sensor may also be operated without a DC power source. Operation of the sensor seen in FIG. 2 without a DC power source is desirable in that such a power source will cause noble metal catalysts in protonic conductive membrane 12 to coalesce into larger particles which tends to reduce long term sensor response and detract from the stability of the sensor. Consequently, the small proton resistance of the relatively thin protonic conductive membrane 12 enables the embodiment seen in FIG. 2 to be operated without a DC power source in the measurement of CO gas by sensor 10.

Protonic conductive membrane 12 will preferably be a solid proton conductive electrolyte membrane coated with a catalyst on both sides thereof. The solid proton conductive electrolyte membrane is composed of an organic material, such as a polymer material, or may also be composed of an inorganic material such as a metal oxide. Where the solid protonic conductive electrolyte membrane is an organic membrane, the organic membrane will preferably be a polymer proton conductive material such as NAFION™ 117, or XUS-1304.10 membrane. NAFION is manufactured by DuPont and XUS is manufactured by Dow Chemical Co. of the United States of America. Alternatively, the organic material may be a R4010-55 membrane supplied by PALL RAI Co., also of the United States of America.

In the inventive sensor design as shown in FIG. 2, it is desirable that both area and thickness parameters are optimized. It is beneficial for CO sensor 10 to have a 0.1 mm-1 mm thick NAFION™ protonic membrane, and that the diameter of sensing and counter electrodes 16, 14 be approximately 1 mm to 15 mm. Preferably, CO sensor 10 has a 0.17 mm thick NAFION™ protonic membrane or the like with 10 mm diameter sensing and counter electrodes 16, 14, which results in a bulk ionic resistance of 1.0 ohm. The proton conductor for both the sensing and counter electrodes is preferably a copolymer based on a tetrafluoroethylene backbone with a side chain of perfluorinated monomers containing sulfonic or carboxylic acid groups, especially a NAFION™ 117 material from DuPont, or a R4010-55™ material from Pall RAI Manufacture Co., or the like.

Where the solid proton conductor of electrolyte membrane is composed substantially of inorganic materials, such as a metal oxide proton conductive material, then it is preferable that the metal oxide proton conductive material be $Sb_2O_5.4H_2O$ as a composition of materials.

Microporous hydrophobic membrane 204 will preferably be an organic material such as CELGARD 2400™ supplied by Celanese Corporation of the United States of America. Alternatively, microporous hydrophobic membrane 204 may also be a GORETEX™ membrane supplied by W. L. Gore & Associates, Inc. of the United States. Alternatively, microporous hydrophobic membrane 204 may also be a ZITEX™ membrane supplied by Norton Performance Plastics Corporation, also of the United States of America.

Preferably, counter electrode 14 and sensing electrode 16 will have a thickness of approximately 0.1 mm and a diameter of approximately 13 mm. Also preferably, hole 202 will have a diameter of 3 mm and hole 206 will have a diameter of 0.2 mm, each hole being in the center of its respective piece. Preferably, microporous hydrophobic membrane 204 will have a thickness of 0.1 mm and a diameter of 10 mm. Preferably, protonic conductive membrane 12 will have a thickness of 0.1 mm and a diameter of 20 mm. It is preferable that protonic conductive membrane 12 be less than 1 mm in thickness so that the resistance of the same will be desirably low. It is desirable to have a small proton resistance so that the proton electrical current that is generated as a result of pressure differences of the target gas CO across protonic conductive membrane 12 without applying a DC power. The background electrical current will be preferably in the nA range or less, which is negligible.

Figure 6:
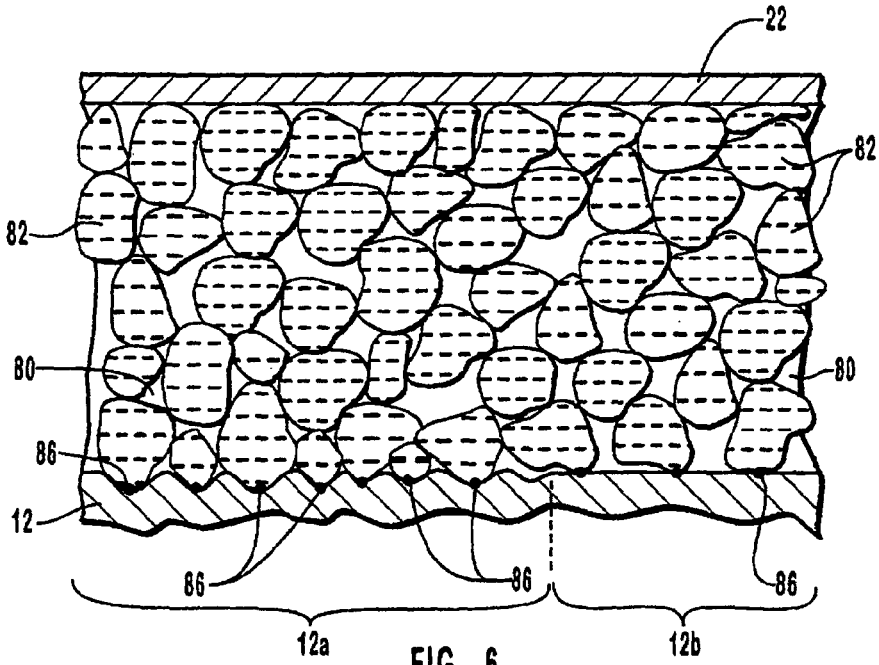
FIG. 6 shows an electrically conductive thin electrically conductive film electrode, permeable to water vapor, in contact with a current collector, and a protonic conductive membrane having either a planar or nonplanar interface, including electron conductive phases, gas phases, and three-phase contact areas.

As an alternative to manufacturing counter electrode 14 and sensing electrode 16 from mixed protonic electronic conductive materials, a thin film of electrically conductive film, such as noble metal film which is deposited upon protonic conductive membrane 12, may also be used in replacement for such electrodes. Preferably, the thin metal film will be deposited by sputtering or physical vapor deposition, or other known methods of depositing a thin metallic film, where the film is permeable to water vapor. Such a film is seen in FIG. 6, discussed below.

The purpose of the noble metal thin film is to generate a chemical reaction by acting as a catalyst and for conducting electrons through a very thin distance provided by the deposited layer of thin noble metal film. The thin noble metal film is in contact with the protonic conductive membrane which conducts protons therethrough. By minimizing the distance through which electrons are conducted by the thin noble metal film, and selecting the thin noble metal film to be an excellent electron conductor, then the sensor is made most efficient in transferring both electrons and protons therethrough in the process of detecting CO concentration in the ambient. Preferably, the noble metal thin film will be in the range of about 50 Angstroms to about 5,000 Angstroms. By way of example, platinum or palladium are suitable noble metal films. It is preferable that the catalyst be a good electron conductor while the protonic conductive membrane be a good proton conductor.

The sensor depicted in FIG. 2 may also be constructed and used without applying a DC power. This is particularly true in that a sensor constructed according to that depicted in FIG. 2 absent the electrical circuitry, has a small proton resistance. The proton current generated as a result of the pressure difference of the target gas across the membrane is strong enough to be detected without applying a DC power. In such an embodiment of the inventive sensor, the background current is in the nA range or less, which is basically negligible. Operating the sensor of FIG. 2 without applying a DC power is advantageous in that it lends long term stability in the performance of the inventive sensor. This is true in that the particle size of the noble metal catalyst of the electrodes to the inventive sensor do not coalesce when there is no DC power applied. As such, the maintenance of the small particle size of the noble metal catalyst in the electrode prevents the reduction of the long term functionality and accuracy of the inventive sensor response.

Protonic conductors membranes are usually slightly permeable to CO gas. When a membrane is under a carbon monoxide partial pressure difference, a very small amount of carbon monoxide will permeate across the membrane into the counter electrode side.

Influence of the CO permeation to sensor response usually is insignificant because this very small amount of permeated CO is instantly converted into carbon dioxide at the reference electrode. If a precision CO concentration detection is needed, CO concentration in the counter electrode can be minimized by attaching an electrochemical CO pump to the sensor according to this invention. The purpose of an electrochemical pumping circuitry is to prevent the buildup of CO gas at the counter electrode side of the sensor so that a precision CO detection is achieved.

Protonic conductive membrane 12 may be substantially composed of a solid, perfluorinated ion-exchange polymer, or a metal oxide protonic conductor electrolyte material. The following table serves as a further example of solid state protonic conductor which can be used at room temperature in the inventive gas sensor.

| MATERIALS | | |
|---|---|---|
| 1. $H_3Mo_{12}PO_{40}\bullet 29H_2O$ | 6. NAFION ™ | DuPont . (US) |
| 2. $H_3W_{12}PO_4\bullet 29H_2O$ | 7. C membrane | Chlorine Engineer's (Japan) |
| 3. $HUO_2PO_4\bullet 4H_2O$ | 8. XUS-1304.10 | Dow (US) |
| 4. $Zr(HPO_4)_2\bullet 3H_2O$ | 9. R4010-55 | PALL RAI Manufacturing Co. (US) |
| 5. $Sb_2O_5\bullet 4H_2O$ | | |

Protonic conductive membrane 12 is preferably constructed of materials 6, 7, 8, or 9 which are unreinforced film of perfluroinated copolymers.

Figure 3:
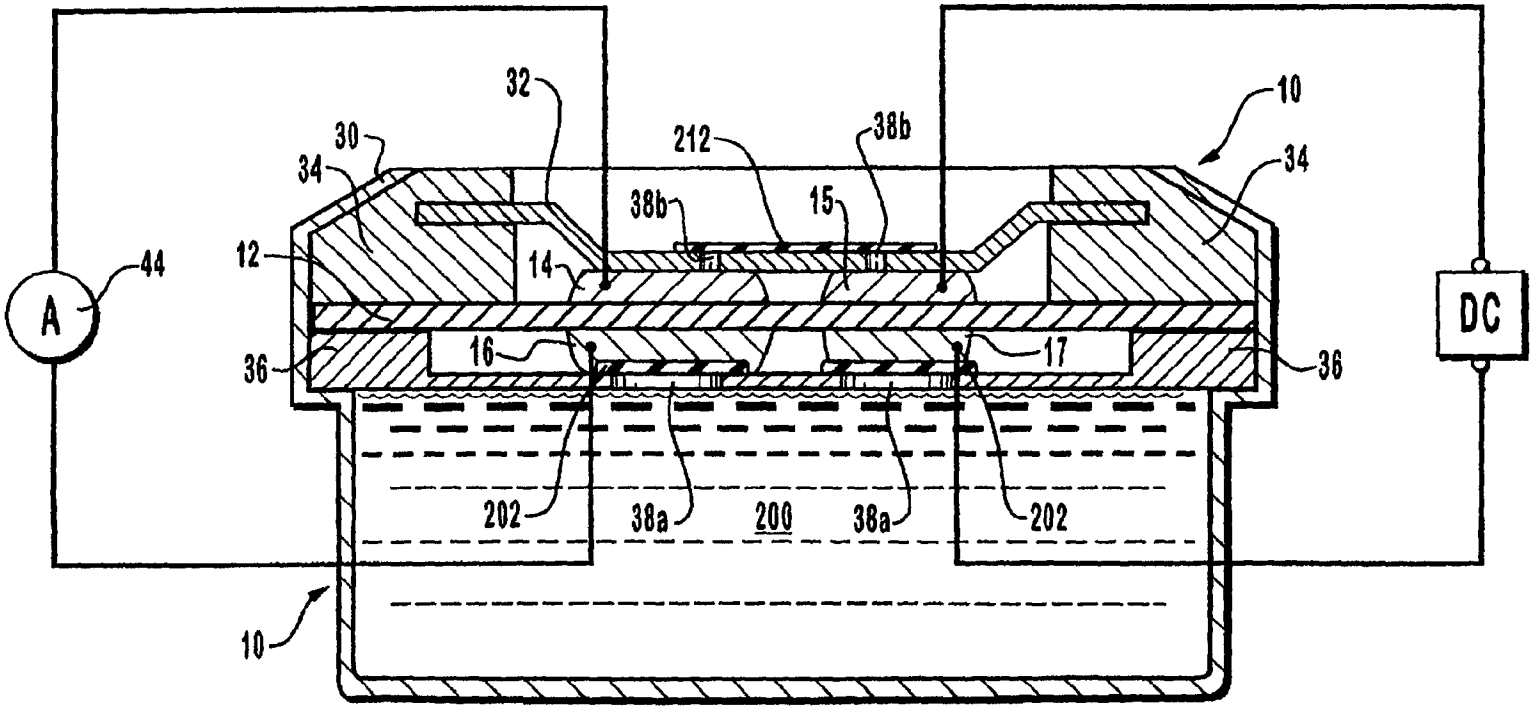
FIG. 3 shows an alternative embodiment of the inventive electrochemical sensor, further featuring a water reservoir and a CO pump structure. The electrochemical sensor depicted in FIG. 4 has four electrodes attached to a protonic conductive membrane, two of which are normal sensing and counter electrodes, and the other two electrodes are used to pump permeated CO out of the counter electrode side of the electrochemical cell. In this alternative embodiment of the inventive CO sensor, DC power can be applied in either a pulse mode or a constant mode. The electrochemical sensor is enclosed within an electrically insulated cap and can design.

FIG. 3 features counter numerals similar to FIG. 2, with identical counter numerals referring to similar structures performing similar functions. FIG. 3 shows an alternative embodiment of sensor 10. An amperometric measuring unit 44 is in electrical communication with electrodes 14, 16, and DC power switching circuity is shown in electrical communication with a pair of pump electrodes 15, 17. All of the electrodes 14-17 are interfacing with protonic conductive membrane 12. The purpose of pump electrodes 15, 17 is to continuously pump CO away from counter electrode 14 side of sensor 10 while continuously sensing the presence of CO gas in the ambient. This continuous pumping of CO away from the side of sensor 10 where counter electrode 14 is located serves to give stability to the sensor signal response to CO concentration in the ambient. The DC power source can be operated in either "pulse" mode to pump CO, or in the "on" mode to sense CO concentration. In sensor 10, depicted in FIG. 3, both can 30 and cap 32 are preferably made of electrically insulative materials.

Large holes 38a in washer 36 expose a larger surface area of reference electrode 16 to water vapor in reservoir 200 than the surface area of sensing electrode 14 and count electrode 15 exposed to ambient atmosphere. As such, protonic conductive membrane 12 and all electrodes are exposed to substantially 100 percent relative humidity, and a positive pressure of the water vapor in reservoir 200 exists from each hole 38a to each hole 38b due to the partial pressure difference therebetween.

Figure 4:
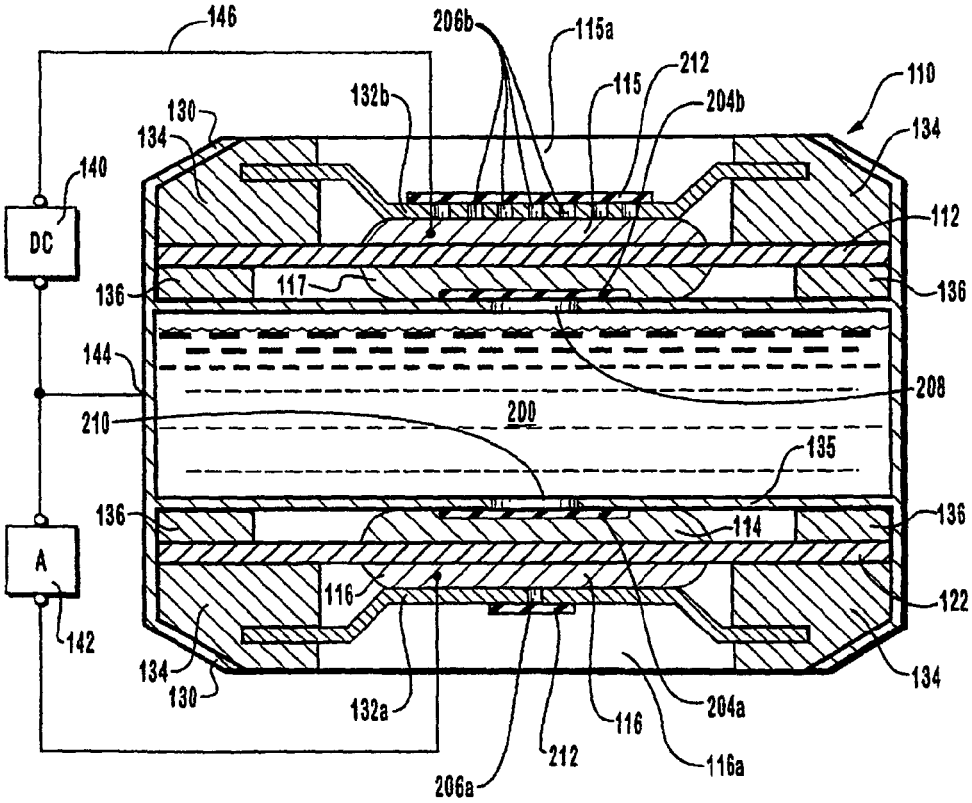
FIG. 4 shows a further embodiment of the inventive electrochemical CO sensor, having two protonic conductive membranes, the first membrane being used to sense CO, and the second membrane being used to pump permeated CO out of the counter electrode side of the electrochemical CO sensor. A de-ionized water reservoir in the middle of the sensor is separated on each side thereof from the first and second membranes by a microporous hydrophobic filter and an electrode.

A further embodiment of the inventive CO sensor is seen in FIG. 4 as a sensor 110. Sensor 110 has two protonic conductive membranes 112, 122 that prevent interference with the response of sensor 110 due to the detection of CO concentrations. Sensor 110 features a can 130 having water reservoir 200 therein.

Can 130 is an example and illustration of a means, containing a volume of water vapor, for exposing a surface of a counter electrode to the water vapor. Upon such exposure to an atmosphere concentration of a gas, such as CO, electrical measurements can be made to detect changes in electrical characteristics of the electrodes.

Material 134 and washer 136 retains first and second protonic conductive membranes 122, 112 within can 130. A sensor electrode 116 is on an opposite side of first protonic conductive membrane 122 from a counter electrode 114. First and second pump electrodes 115, 117 are in contact with opposite sides of second protonic conductive membranes 112. A bottom cap 132A and a top cap 132B have holes therein, respectively, having holes 206a, 206b. Can 130 has large holes 210, 208 therein.

Due to the geometric of holes 206a, 206b, 208, and 210, there will be a greater exposed surface area of first pump electrode 115 to the ambient than the surface area of sensing electrode 116 exposed to the ambient. Consequently, protonic conductive membrane 112 is exposed to substantially 100 percent relative humidity.

A DC power source 140 is in electrical contact with first pump electrode 115 and metallic can 130 through electrical contacts 146 and 144. DC power source 140, and related circuity, serve as an example of a means for applying a DC power across the protonic electrolyte membranes. Sensing electrode 116 is in contact with an electrical measurement means 142 through electrical leads 146, 144. DC power supply 140 serves as a CO pump to sensor 110. By way of example and illustration of an electrical sensing means, a meter 142 is used to measure the response of sensor 110 to concentrations of CO.

Sensing electrode 116 is exposed to the ambient through hole 206a via microporous hydrophobic dust filter 212. First pump electrode 115 is exposed to the ambient atmosphere holes 206b, where the area between reservoir 200 and membrane 122 serves as a counter environment for electrode 114.

Sensing electrode 116, exposed to the ambient atmosphere through holes 206a, with first protonic conductive membrane 122 performs the function, in combination with counter electrode 114 of sensing CO concentration through the conduction therethrough of protons. Second protonic conductive membrane 112, in combination with first and second pump electrodes 115, 117, performs the function of pumping CO out of the side of sensor 110 associated with counter electrode 114 so as to stabilize the sensor response of sensor 110 upon the detection of a concentration of CO in the ambient.

Figure 5A:
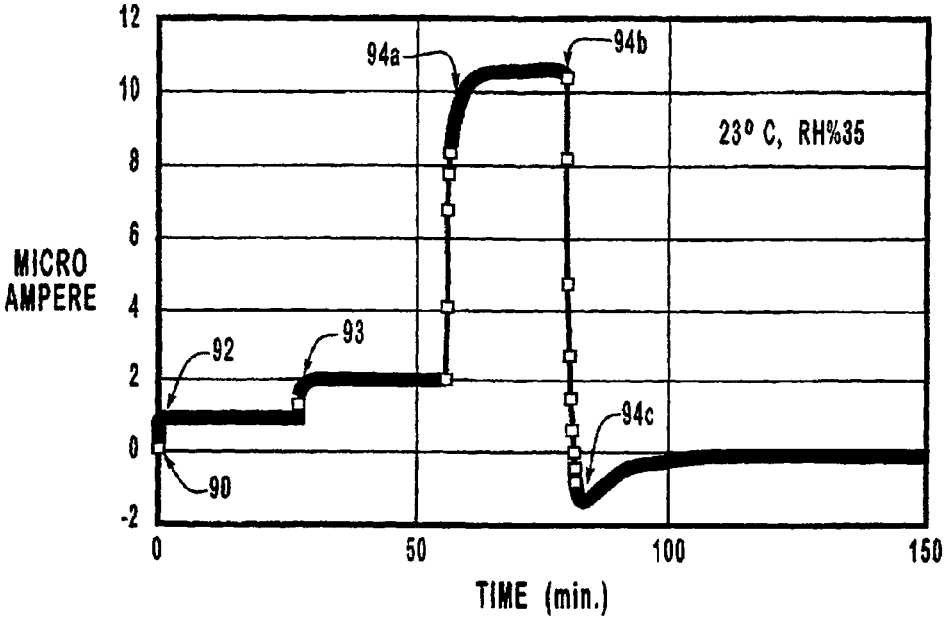
FIG. 5A depicts the inventive sensor electrical current output over time in an atmosphere of constant temperature and relative humidity with increasing CO concentration.

FIG. 5A shows sensor voltage response with respect to time of the inventive one protonic conductive membrane gas sensor seen in FIG. 2. Reference point 90 shows zero time with a negligible CO concentration. Reference point 92 shows an environment of 100 ppm CO after a period of less than one minute. At reference point 93 on FIG. 5A, an injection of 200 ppm CO is made into the environment such that sensor responses maximizes at reference point 94a on FIG. 5A. At reference point 94b on FIG. 5A, the atmosphere is seen to be opened up to clean air and the sensor response decreases by a slight under shoot to reference point 94c on FIG. 5A after a period of about one minute. The senor response levels back to zero amps as time goes on from reference point 94c. FIG. 5A reflects environmental parameters of 23° C. and 35% relative humidity. Such a sensor current response is seen in a nonlogrithmic scale in FIG. 5B.

Figure 5B:
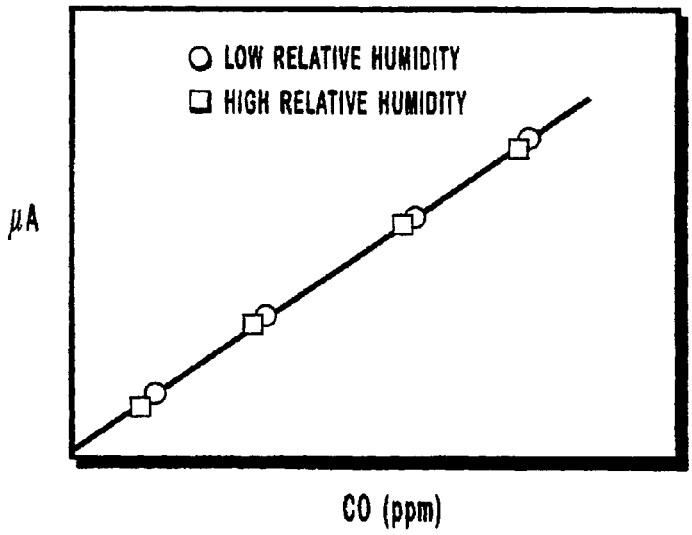
FIG. 5B depicts the inventive sensor electrical current output in increasing CO concentration at dual relative humidity.

FIG. 5B shows the characteristic of the inventive CO sensor with respect to its independence of varying relative humidity environments. In an amperometric embodiment of the inventive CO gas sensor, as can be seen from FIG. 5B, relative humidity does not interfere with the linear nature of the sensor response in increasing environments of CO concentration. The ability of the inventive amperometric CO sensor to avoid interference with relative humidity is that, because of the water vapor contained in the housing of sensor and the exposure of the protonic conductive membrane to the water vapor, the protonic conductive membrane is constantly in a state of saturation regardless of ambient atmospheric relative humidity. Thus, bulk ionic resistance of the inventive CO sensor is constant as relative humidity changes. Electrical current, which is the measurement of sensor response, also remains constant.

In the inventive CO sensor, the sensing electrode is exposed to an environment containing CO, whereas the sensing electrode, counter electrode side and proton conductor are exposed to a 100 percent relative humidity environment. The protonic conductive membrane can have the thickness so that the reactant oxygen and the produced water permeate the membrane. A small part of CO gas also permeates through the membrane, but the permeated CO is consumed by the reaction with oxygen electrochemically and catalytically at the counter electrode.

Figure 7:
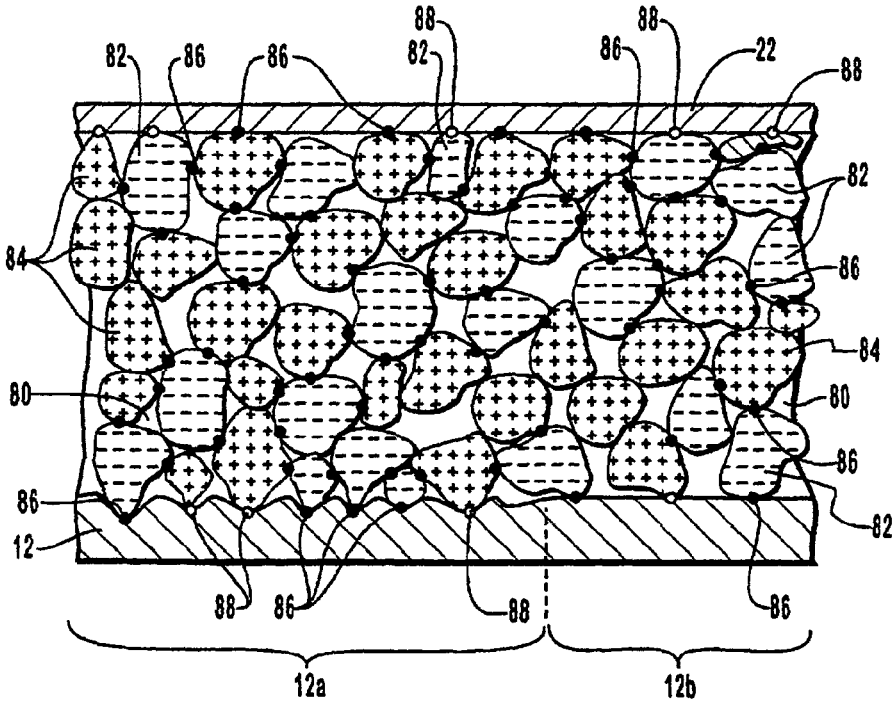
FIG. 7 shows a mixed protonic-electronic conductive electrode, permeable to water vapor, the electrode being shown in contact with a current collector, and a protonic conductive membrane having either a planar or a nonplanar interface in amplified view of the materials therein having protonic and electronic conductive phases, gas phases, and three-phase contact areas.

Alternative embodiments of the inventive sensor are depicted in FIGS. 6 and 7, where the protonic conductive membrane is seen in two parts. Particularly a nonplanar surface of protonic conductor membrane 12 is seen at portion 12a thereof. A planar surface of protonic conductor membrane 12 is seen in portion 12b thereof. By increasing the surface area of portion 12a via a nonplanar surface, greater contact with the materials of the catalyzing and electrical conducting electrode thereover is possible. A greater contact will ensure a greater conductivity of protons and electrons therethrough as well as a greater surface upon which to catalyze. The creation of such a nonplanar surface may be accomplished by a chemical or physical abrasion process, or by other known method.

FIG. 6 illustrates an example of an electrode made of an electrically conductive thin film situated upon a protonic conductive membrane. The film has an average thickness in the range of about 50 Angstroms to 10,000 Angstroms, and will preferably be in the range of about 4,000 Angstroms to 6,000 Angstroms. The preferable film is substantially composed of a noble metal, such as platinum. The film may be deposited on protonic conductive membrane 12 by sputter, or by vapor deposition techniques, or by other known film layering techniques.

FIG. 6 is an amplified view of an electrically conductive electrode having protonic conductive membrane 12, a current collector electrical lead 22, and an electron conductive phase material 82 therebetween. Electron conductive phase material 82 has a plurality of gaps 80 interstitially placed between particles of electron conductive phase material 82. A plurality of three-phase contact areas 86 exists and interfaces between protonic conductive membrane 12 and electron conductive phase material 82. CO gas in the ambient coming in contact with electron conductive phase material 82 produces electrons which are drawn to current collector electrical lead 22. CO gas in the ambient coming in contact with the interface of electron conductive phase material 82 and protonic conductive membrane 12 at three-phase conductive contact area 86 will produce hydrogen ions, or protons, which are conducted through protonic conductive membrane 12. As can be seen from FIG. 6, the creation of hydrogen ions occurs only at the surface of protonic conductive membrane 12 at three-phase contact area 86. Thus, there is limited surface at which the creation of hydrogen ions can take place in the embodiment of the electronically conducted electrode shown in FIG. 6.

FIG. 7 shows a mixed protonic-electronic conductive electrode having a protonic conductive membrane 12, a current collector electrical lead 22, and a variety of amplified particles therebetween and consisting of an electronic conductive phase material 82, and a protonic conductive phase material 84. Between particles of protonic conductive phase material 84 and electronic conductive phase material 82, there are gaps 80 which represent the pores between the particles situated between current collector electrical lead 22 and protonic conductive membrane 12. Electrons are transmitted to current collector electrical lead 22 when CO gas in the ambient comes in contact with three-phase contact area 86. Hydrogen ions are transported to protonic conductor membrane 12 when CO gas in the ambient comes in contact with three-phase contact area 86. The creation of both hydrogen ions and electrons occurs at each of the plurality of three-phase contact areas 86 shown in FIG. 7. Neither electrons nor hydrogen ions are created at interface 88 which is situated between protonic conductive membrane 12 and protonic conductive phase material 84. Similarly, no reaction to create electrons or hydrogen ions occurs at an interface 88 between current collector electric lead 22 and electronic conductor phase material 82.

As can be seen from FIG. 7, the creation of hydrogen ions occurs in the three-dimensional area between current collector electrical lead 22 and protonic conductive membrane 12. Thus, the surface area available to create hydrogen ions is greater in the electrodes seen in FIG. 7 as compared to the electrode seen in FIG. 6. This additional surface area for creation of hydrogen ions is due to the presence of protonic conductive phase material 84 in the electrode above protonic conductive membrane 12. Conversely, FIG. 6 does not contain any protonic conductive phase material situated on and above protonic conductive membrane 12.

The mixed conductor material found in the electrode seen in FIG. 7 has desirable benefits, such as provision of a high surface area for the CO oxidation reaction in the sensing electrode side, and providing a high surface area for the $H_2O$ formation reaction in counter electrode side. The thin film of the electrode seen in FIG. 6, while being an efficient conductor of electrons, also provides a short path for protonic conduction, which tends to be faster than a thicker electrically conductive electrode that does not conduct protons efficiently. The inventive alcohol sensor based on FIG. 7 shows large response to alcohol, and the inventive CO sensor based on FIG. 6 shows almost zero interference by other gases. As can be seen either electrode embodiment of FIGS. 6 or 7 can be beneficial. Proton conductive membrane 12 is indicated in both FIGS. 6 and 7 as having either a substantially non-planar interface 12a, or a substantially planar interface 12b. As such, it is intended that any of the electrodes of the inventive sensor, in any of the disclosed embodiments herein, may be either a mixed proton electron conductor material electrode or may be a thin film electron conductor material electrode. Further, mixed conductor and thin film electrodes may been used in any combination thereof within any embodiment of the inventive sensor.

Figure 8:
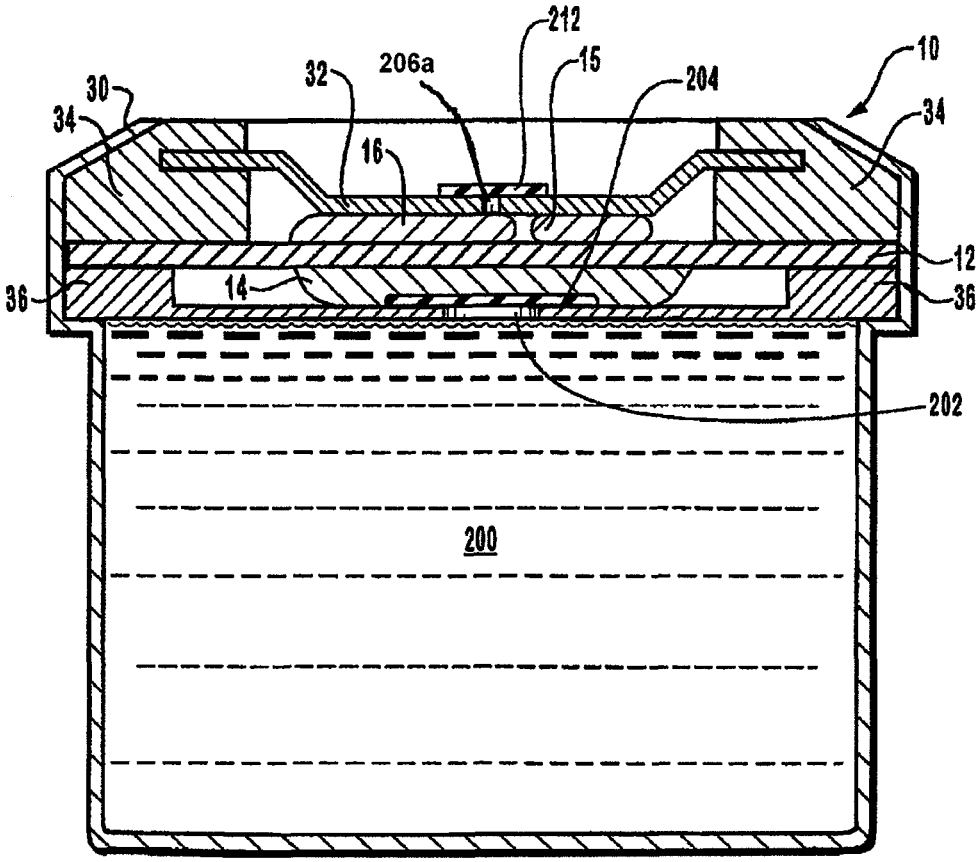
FIG. 8 is an alternative embodiment of the inventive gas sensor having a water reservoir and three electrodes which are a sensing electrode, a count electrode, and a reference electrode.

FIG. 8 depicts an embodiment of the inventive sensor having three electrodes. While the foregoing embodiments of the inventive sensor used only two electrodes, and thereby resulted in cost savings, a three-electrode embodiment of the invention is seen as sensor 10 in FIG. 8. Reference numerals in FIG. 8 identical to reference numerals in FIG. 2, represent similar structures performing similar functions.

Sensor 10 in FIG. 8 has a reference electrode 15 and a counter electrode 14 and on an cap 32 on an opposite side of a protonic conductive membrane 12 from a sensing electrode 16. Sensing electrode 16 is vented to the ambient through a small hole 206a that is smaller than a large hole 202 vented to reservoir 200 having water vapor therein. A microporous hydrophobic membrane 204 is positioned in between hole 202 and counter electrode 14. Gasket 36 and a material 34 retain protonic conductive membrane 12 in can 30.

Those of ordinary skill in electrical measurement circuitry may incorporate such circuitry to obtain sensor response in ambient concentrations of a target gas with sensor 10 in FIG. 8, including variations of circuitry disclosure herein.

The inventive CO gas sensor using the mixed protonic-electronic conductive materials in the electrodes with high surface area of 100 to 1000 $M^2/g$ shows a shorting current as high as 150 $\mu A/cm^2$ to 1,000 ppm CO, which is at least two orders of magnitude higher compared to the sensors with electronic conductive electrodes according to prior art.

| COUNTER ELECTRODE | SENSING ELECTRODE |
|---|---|
| A preferred composition of such electrodes is as follows: | |
| 7.5 wt % Ru oxide | 20 wt % Pt-black |
| 67.5 wt % carbon | 55 wt % carbon |
| 25 wt % NAFION ™ | 25 wt % NAFION ™ |
| Other compositions of such electrodes are as follows: | |
| Pd 20 wt % | Pd 20 wt % |
| Carbon 60 wt % | Carbon 60 wt % |
| $Sb_2O_5 \cdot 4H_2O$ 20 wt % | $Sb_2O_5 \cdot 4H_2O$ 20 wt % |
| Rb 25 wt % | Pd 25 wt % |
| Carbon 50 wt % | Ni 50 wt % |
| R4010-55 25 wt % | R4010-55 25 wt % |
| 10 wt % Pt on vulcan carbon | 10 wt % Pt on vulcan carbon |
| XC72 25 wt % | XC72 25 wt % |
| NAFION ™ 25 wt % | NAFION ™ 25 wt % |
| Ti 50 wt % | Ni 50 wt % |
| 20 wt % Pt-Black | 20 wt % Pt-black |
| 55 wt % carbon | 55 wt % carbon |
| 25 wt % NAFION ™ | 25 wt % NAFION ™ |

The role of platinum in the sensing electrode is to favor the CO decomposition reaction (1) whereas Ru oxide in the counter electrode is to favor the water formation reaction (2). According to this invention, the Ru oxide, instead of expensive platinum and the like, as reported in prior art, shows excellent CO sensing performance.

It is also contemplated that the electrodes disclosed herein can be composed substantially of carbon, noble metals, or conductive metal oxides. The electrical conducting material in electrodes disclosed here is preferably a proton-electron mixed conductive material having 10-50 wt % of a proton conductor material and 50-90 wt % of a first and a second electrical conductor material. The proton conductor material for the electrodes disclosed herein is preferably a copolymer having a tetrafluoroethylene backbone with a side chain of perfluorinated monomers containing at least one of a sulfonic acid group or carboxylic acid group. Preferably, one of the first and second electrical conductor materials for the sensing electrodes disclosed herein is 50-99 wt % of carbon black, and the other of the first and second electrical conductor materials for the sensing electrodes disclosed herein is 1-50 wt % of platinum. Also preferably, one of the first and second electrical conductor materials for the counter electrode is 50-99 wt % of carbon black, and the other of the first and second electrical conductor materials for the counter electrode is 1-50 wt % of Ru oxide.

In a composition of 25 wt % protonic conductor in electrodes, which is a physically continuous phase, there is proton conduction, whereas the rest of the phases in electrodes provide electronic conduction as well as catalytic activity. If without 25 wt % proton conductor in electrodes, the electrodes were only an electronic conductor, and the reactions (1) and (2), above, would only occur at three-phase contact area 86 seen in FIG. 6, which is a very limited small area. When the electrodes are made of mixed conductors according to this invention, the reactions (1) and (2) will occur on all surface of the electrodes. Therefore, by using high surface area mixed conductive electrodes (100 to 1,000 $M^2/g$) seen in FIG. 7, fast CO reaction kinetics at the interface are achieved and strong signal response is obtained.

While the inventive gas sensor can be used to measure CO concentration, it is also capable of measuring other gases such as $H_2$, $H_2S$, $H_2O$ vapor alcohol, and $NO_x$ concentrations.

Various protonic conductors, including organic protonic conductors and inorganic protonic conductors, can be used in the sensor according to this invention. In what follows, a copolymer protonic conductive membrane based on a tetrafluoroethylene backbone with a side chain of perfluorinated monomers containing sulfonic acid group is used herein as an example of the fabrication of the inventive sensor.

To prevent deterioration of the polymer membrane in the subsequent wetting/drying steps, the membrane must be first converted from the proton form to the sodium form by the following steps A:

A. The polymer membrane is soaked in lightly boiling dilute NaOH solution for 1-3 hours. It is then rinsed first in tap water for 0.5-3 hours, then in deionized water for 10-30 minutes, and is then laid out on a rack to air dry.

B. The materials for the preferred mixed conduction electrodes are as follows: Pt/carbon powder, carbon powder, Ru oxide powder, solubilized polymer solution, Glycerol, NaOH solution, and deionized water.

C. The steps for fabrication are as follows:
   1. Pre-mix deionized water and glycerol in 20-30% weight ratio, and store the mixture in a container;
   2. Weigh an appropriate amount of Pt/carbon powder into a clean container;
   3. Weigh an appropriate amount of 5% wt polymer solution, and add to material in step C.2, and then mix. Typically, add 1-3 parts 5% wt NAFION™ solution (on a dry polymer basis) to 3-5 parts Pt/carbon powder;
   4. Weigh and add an appropriate amount of water/glycerol mixture to mixture in step C.3, and then mix. Typically, add 25-35 parts water/glycerol mixture to one part Pt/carbon powder;
   5. Weigh and add an appropriate amount of 1-2 Moles NaOH to the mixture in step C.4, and then mix. Typically, add 1-2 parts 1-2 Moles NaOH to 9-15 parts 5% wt polymer solution; and further mix the wet electrode mixture ultrasonically for 60 minutes.

D. For Carbon/Ru Oxide electrode preparation, the following steps are taken:
   1. Pre-mix the deionized water and glycerol in 20-30% weight ratio, store the mixture in a container, and set aside;
   2. Weigh an appropriate amount of carbon powder and Ru oxide into a clean container;
   3. Weigh an appropriate amount of 5% wt polymer solution, and add to the material in step D.2, and then mix. Typically, add 1-3 parts 5% wt polymer solution (on a dry polymer basis) to 3-5 parts carbon/Ru oxide powder;
   4. Weigh and add an appropriate amount of water/glycerol mixture to mixture in step D.3, and then mix. Typically, add 25-35 parts water/glycerol mixture to 1 part carbon/Ru oxide powder;
   5. Weigh and add an appropriate amount of 1-2 Moles NaOH to the mixture in step C.4, and then mix. Typically, add 1 part 1-2 Moles NaOH to 9-15 parts 5% wt polymer solution; and further mix the wet electrode mixture ultrasonically for 60 minutes.

E. For Pt/Carbon Electrode application drying, the following steps are taken:
   1. Re-mix the wet electrode mixture ultrasonically for at least 30 minutes prior to use;
   2. Fill the dispensing machine tubing with the Pt/carbon wet electrode mixture;
   3. Dispense the wet electrode mixture to the surface of the membrane at the desired location; and
   4. Place the membrane/electrode in an oven at 100°-170° C. for 10-60 minutes.

F. For Carbon/Ru Oxide Electrode application drying, the following steps are taken:
   Repeat step A on the opposite side of the membrane.

G. For acidification, the following steps are taken:
   1. For Ion-Exchange, soak membrane/electrodes in lightly boiling dilute MH2S04 solution for 1-3 hours.
   2. For cleaning, rinse the membrane/electrodes in deionized water;
   3. For drying, dry the membrane/electrodes in air, or air dry then desiccate overnight, or place in a 30°-50° C. oven for 1-3 hours before cutting to the final dimensions.

The present invention may be embodied in other specific forms without departing from its spirit or essential characteristics. The described embodiments are to be considered in all respects only as illustrated and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. An electrochemical gas sensor for quantitative measurement of a gas in a ambient atmosphere comprising:

a sensing electrode permeable to water vapor and comprised of an electrical conducting material and having a surface exposed to the ambient atmosphere;

a counter electrode permeable to water vapor and comprised of an electrical conducting material;

a first protonic conductive electrolyte membrane permeable to water vapor and situated between and in contact with the sensing and counter electrodes, the sensing electrode reacting with the gas to produce a change in electrical characteristic between the sensing electrode and the counter electrode;

means for electrical measurement electrically connected to said sensing and counter electrodes;

means, containing a volume of water vapor, for exposing a surface of said counter electrode to said water vapor, wherein the electrical conducting material of at least one of said sensing and counter electrodes is a proton-electron mixed conductive material having 10-50 wt % of a proton conductor material and 50-90 wt % of a first and a second electrical conductor material; whereby, in a positive ambient atmosphere concentration of said gas, said electrical measurement means detects changes in said electrical characteristic.

2. The electrochemical gas sensor as defined in claim 1, wherein said water vapor containing means contains a volume of water and an antifreeze additive.

3. The electrochemical gas sensor as defined in claim 1, wherein the surface of said sensing electrode that is exposed to the ambient atmosphere has a surface area that is smaller than the surface area of the surface of the counter electrode that is exposed to said water vapor, whereby the first protonic conductive electrolyte membrane is exposed to substantially 100 percent relative humidity, and a positive pressure of said water vapor exists from the surface of said counter electrode exposed to said water vapor to the surface of said sensing electrode exposed to the ambient atmosphere.

4. The electrochemical gas sensor as defined in claim 3, wherein the surface area of the surface of the counter electrode that is exposed to said water vapor is separated from said means for exposing a surface of said counter electrode to said water vapor by a hydrophobic membrane permeable to water vapor and substantially impervious to water.

5. The electrochemical gas sensor as defined in claim 1, wherein the first protonic conductive electrolyte membrane has opposing surfaces, each of said opposing surfaces being in contact with one of the sensing and counter electrodes, wherein at least one of the opposing surfaces of said first protonic conductive electrolyte membrane in contact with one of the sensing and counter electrodes is substantially nonplanar.

6. The electrochemical gas sensor as defined in claim 1, wherein at least one of the sensing and counter electrodes is comprised of film having a thickness in the range of about 50 Angstroms to 10,000 Angstroms.

7. The electrochemical gas sensor as defined in claim 6, wherein the film is substantially composed of a noble metal.

8. The electrochemical gas sensor as defined in claim 7, wherein the noble metal is platinum.

9. The electrochemical gas sensor as defined in claim 1, wherein the first protonic conductive electrolyte membrane is substantially composed of a solid, perfluorinated, ion-exchange polymer.

10. The electrochemical gas sensor as defined in claim 1, wherein the first protonic conductive electrolyte membrane is a hydrated metal oxide protonic conductor electrolyte membrane.

11. The electrochemical gas sensor as defined in claim 1, wherein the proton conductor material for said at least one of the sensing and counter electrodes is a copolymer having a tetrafluoroethylene backbone with a side chain of perfluorinated monomers containing at least one of a sulfonic acid group or a carboxylic acid group.

12. The electrochemical gas sensor as defined in claim 1, wherein one of the first and second electrical conductor materials for said at least one of the sensing and counter electrodes is about 50-99 wt % of carbon black, and the other of the first and second electrical conductor materials for said at least one of the sensing and counter electrodes is about 1-50 wt % of platinum.

13. The electrochemical gas sensor as defined in claim 1, wherein one of the first and second electrical conductor materials for said at least one of the sensing and counter electrodes is about 50-99 wt % of carbon black, and the other of the first and second electrical conductor materials for said at least one of the sensing and counter electrodes is about 1-50 wt % of Ru oxide.

14. The electrochemical gas sensor as defined in claim 1, wherein the electrochemical gas sensor further comprises:

first and second pump electrodes comprised of an electrical conducting material permeable to water vapor, separate from said sensing and counter electrodes, and situated on opposite sides of and in contact with said first protonic conductive electrolyte membrane, said second pump electrode being situated on the same side of said first protonic conductive membrane as the counter electrode and having a surface thereon exposed to the water vapor in said means for exposing a surface of said counter electrode to said water vapor; and means for applying a DC power across the first protonic conductive electrolyte membrane, said first and second pump electrodes having in electrical connection therebetween said means for applying DC power across the first protonic conductive electrolyte membrane;

whereby the gas is transported away from the counter electrode when the DC power means applies a DC power to the first and second pump electrodes.

15. The electrochemical gas sensor of claim 14, wherein the electrical conducting material of the first and second pump electrodes is substantially composed of carbon.

16. The electrochemical gas sensor as defined in claim 14, wherein the electrical conducting material of the first and second pump electrodes is substantially composed of noble metals.

17. The electrochemical gas sensor as defined in claim 14, wherein the electrical conducting material of the first and second pump electrodes is substantially composed of conductive hydrated metal oxides.

18. The electrochemical gas sensor as defined in claim 14, wherein at least one of the first and second pump electrodes is comprised of a film having a thickness in the range of about 50 Angstroms to 10,000 Angstroms.

19. The electrochemical gas sensor as defined in claim 14, wherein the electrical conducting material of said first and second pump electrodes is a proton-electron mixed conductive material having 10-50 wt % of a proton conductor material and 50-90 wt % of a first and a second electrical conductor material.

20. The electrochemical gas sensor as defined in claim 19, wherein the proton conductor material for both the first and second pump electrodes is a copolymer having a tetrafluoroethylene backbone with a side chain of perfluorinated monomers containing at least one of a sulfonic acid group or a carboxylic acid group.

21. The electrochemical gas sensor as defined in claim 19, wherein one of the first and second electrical conductor materials for the first pump electrode is about 50-99 wt % of carbon black, and the other of the first and second electrical conductor materials for the first pump electrode is 1 to 50 wt % of platinum.

22. The electrochemical gas sensor as defined in claim 19, wherein one of the first and second electrical conductor materials for the second pump electrode is about 50-99 wt % of carbon black, and the other of the first and second electrical conductor materials for the second pump electrode is 1 to 50 wt % of Ru oxide.

23. The electrochemical gas sensor as defined in claim 1, wherein the electrochemical gas sensor further comprises:

a second protonic conductive electrolyte membrane permeable to water vapor;

first and second pump electrodes permeable to water vapor and comprised of an electron conductive material, and being separate from said sensing and counter electrodes and situated on opposite sides of and in contact with said second protonic conductive electrolyte membrane, said means for exposing a surface of said counter electrode to said water vapor exposing a surface of said second pump electrode to said water vapor, and said first pump electrode having a surface exposed to the ambient atmosphere; and means for applying a DC power across said second protonic electrolyte membrane, said first and second pump electrodes having in electrical connection therebetween said means for applying DC power across said second protonic electrolyte membrane;

whereby the gas is transported away from the counter electrode when the DC power means applies a DC power to the first and second pump electrodes.

24. The electrochemical gas sensor as defined in claim 23, wherein the second protonic conductive electrolyte membrane is substantially composed of a solid, perfluorinated, ion-exchange polymer.

25. The electrochemical gas sensor as defined in claim 23, wherein the second protonic conductive electrolyte membrane is a hydrated metal oxide protonic conductor electrolyte membrane.

26. The electrochemical gas sensor as defined in claim 23, wherein the surface area of the surface of said first pump electrode that is exposed to the ambient atmosphere is smaller than the surface area of the surface of the second pump electrode that is exposed to said water vapor, whereby the second protonic conductive electrolyte membrane is exposed to substantially 100 percent relative humidity, and a positive pressure of said water vapor exists from the surface of said second pump electrode that is exposed to said water vapor to the surface of said first pump electrode that is exposed to the ambient atmosphere.

27. The electrochemical gas sensor as defined in claim 26, wherein the surface area of the surface of the second pump electrode that is exposed to said water vapor is separated from said means for exposing a surface of said counter electrode to said water vapor by a hydrophobic membrane permeable to water vapor and substantially impervious to water.

28. The electrochemical gas sensor as defined in claim 1, further comprising:

means for applying a DC pulse power source across the first protonic conductive membrane, said sensing and counter electrodes having in electrical connection therebetween said means for applying DC pulse power across the first protonic conductive membrane; and switch means for alternating the connection between the sensing and counter electrodes from the electrical measurement means to the DC pulse power means;

whereby, in a positive ambient atmosphere concentration of said gas, said electrical measurement means detects changes in said electrical characteristic when said switch means connects said electrical measurement means to the sensing and counter electrodes; and whereby said DC pulse power means moves the gas away from a side of the gas sensor where the counter electrode is placed when said switch means connects said DC pulse power means to the sensing and counter electrodes.

29. The electrochemical gas sensor as defined in claim 1, wherein the gas is CO.

30. The electrochemical gas sensor as defined in claim 1, wherein the gas is $NO_x$.

31. The electrochemical gas sensor as defined in claim 1, wherein the gas is hydrogen.

32. The electrochemical gas sensor as defined in claim 1, wherein the gas is $H_2S$.

33. The electrochemical gas sensor as defined in claim 1, wherein the gas is $H_2O$ vapor.

34. The electrochemical gas sensor as defined in claim 1, wherein the gas is alcohol vapor.

35. An electrochemical gas sensor for quantitative measurement of a gas in an ambient atmosphere comprising:

a sensing electrode permeable to water vapor and comprised of an electrical conducting material and having a surface exposed to the ambient atmosphere;

a counter electrode permeable to water vapor and comprised of an electrical conducting material;

a first protonic conductive electrolyte membrane permeable to water vapor and situated in between and in contact with the sensing and counter electrodes, the sensing electrode reacting with the gas to produce a change in electrical characteristic between the sensing electrode and the counter electrode;

a second protonic conductive electrolyte membrane permeable to water vapor;

first and second pump electrodes permeable to water vapor and comprised of an electrical conductive material, and being separate from said sensing and counter electrodes and situated on opposite sides of and in contact with said second protonic conductive electrolyte membrane;

means, containing a volume of water vapor, for exposing a surface of said second pump electrode to said water vapor, and said first pump electrode having a surface exposed to the ambient atmosphere, said second pump electrode being separated from said counter electrode by said means for exposing a surface of said second pump electrode to said water vapor, and said counter electrode having a surface exposed to said water vapor by said means for exposing a surface of said second pump electrode to said water vapor;

means for electrical measurement in electrical communication with said sensing electrode and said counter electrode; and means for applying a DC power across said second protonic electrolyte membrane in electrical contact with said first and second pump electrodes;

whereby the gas is transported away from the counter electrode when the DC power means applies a DC power across said second protonic electrolyte membrane; and whereby, in a positive ambient concentration of said gas, said electrical measurement means detects changes in said electrical characteristic.

36. The electrochemical gas sensor as defined in claim 35, wherein at least one of said first and second protonic conductive electrolyte membranes is substantially comprised of a solid, perfluorinated, ion-exchange polymer.

37. The electrochemical gas sensor as defined in claim 35, wherein at least one of the first and second protonic conductive electrolyte membranes is a hydrated metal oxide protonic conductor electrolyte membrane.

38. The electrochemical gas sensor as defined in claim 35, wherein the surface of said first pump electrode that is exposed to the ambient atmosphere has a surface area smaller than the surface area of the surface of the second pump electrode that is exposed to said water vapor, and wherein the surface of said sensing electrode that is exposed to the ambient atmosphere has a surface area smaller than the surface area of the surface of the counter electrode that is exposed to said water vapor, whereby the first protonic conductive electrolyte membrane is exposed to substantially 100 percent relative humidity, a positive pressure of said water vapor exists from the surface of said counter electrode that is exposed to said water vapor to the surface of said sensing electrode that is exposed to the ambient atmosphere, the second protonic conductive electrolyte membrane is exposed to substantially 100 percent relative humidity, and a positive pressure of said water vapor exists from the surface of said second pump electrode that is exposed to said water vapor to the surface of said first pump electrode that is exposed to the ambient atmosphere.

39. The electrochemical gas sensor as defined in claim 38, wherein the surface area of each of the surfaces of the second pump and counter electrodes that are exposed to said water vapor by said means for exposing a surface of said second pump electrode to said water vapor are each separated from said means for exposing a surface of said second pump electrode to said water vapor by a hydrophobic membrane permeable to water vapor and substantially impervious to water.

40. The electrochemical gas sensor as defined in claim 35, wherein said means for exposing a surface of said second pump electrode to said water vapor further contains an antifreeze additive.

41. The electrochemical gas sensor as defined in claim 35, wherein at least one of the surfaces of said first protonic conductive electrolyte membrane in contact with one of the sensing and counter electrodes is substantially nonplanar, and wherein at least one of the surfaces of said second protonic conductive electrolyte membrane in contact with one of the first and second pump electrodes is substantially nonplanar.

42. The electrochemical gas sensor as defined in claim 35, wherein at least one of the sensing, counter, first pump, and second pump electrodes is comprised of film having a thickness in the range of about 50 Angstroms to 10,000 Angstroms.

43. The electrochemical gas sensor as defined in claim 42, wherein the film is substantially composed of a noble metal.

44. The electrochemical gas sensor as defined in claim 43, wherein the noble metal is platinum.

45. The electrochemical gas sensor as defined in claim 35, wherein the at least one of the sensing, counter, first pump, and second pump electrodes is substantially comprised of proton conductive material.

46. The electrochemical gas sensor as defined in claim 35, wherein at least one of the first and second protonic conductive electrolyte membranes is substantially comprised of a solid, perfluorinated, ion-exchange polymer.

47. The electrochemical gas sensor as defined in claim 35, wherein at least one of the first and second protonic conductive electrolyte membranes is a hydrated metal oxide protonic conductive electrolyte membrane.

48. The electrochemical gas sensor as defined in claim 35, wherein the electrical conducting material of at least one of said sensing, counter, first pump, and second pump electrodes is a proton-electron mixed conductive material having 10-50 wt % of a proton conductor material and 50-90 wt % of a first and a second electrical conductor material.

49. The electrochemical gas sensor as defined in claim 48, wherein the proton conductor material for said at least one of the sensing, counter, first pump, and second pump electrodes is a copolymer having a tetrafluoroethylene backbone with a side chain of perfluorinated monomers containing at least one of a sulfonic acid group or a carboxylic acid group.

50. The electrochemical gas sensor as defined in claim 48, wherein one of the first and second electrical conductor materials for said at least one of the sensing, counter, first pump, and second pump electrodes is about 50-99 wt % of carbon black, and the other of the first and second electrical conductor materials for said at least one of the sensing, counter, first pump and second pump electrodes is about 1-50 wt % of platinum.

51. The electrochemical gas sensor as defined in claim 48, wherein one of the first and second electrical conductor materials for said at least one of the sensing, counter, first pump, and second pump electrodes is about 50-99 wt % of carbon black, and the other of the first and second electrical conductor materials for said at least one of the sensing, counter, first pump, and second pump electrodes is about 1-50 wt % of Ru oxide.

52. An electrochemical gas sensor for quantitative measurement of a gas in an ambient atmosphere comprising:

a sensing electrode permeable to water vapor and comprised of an electrical conducting material and being exposed to the ambient atmosphere;

a reference electrode permeable to water vapor and comprised of an electrical conducting material;

a counter electrode permeable to water vapor and comprised of an electrical conducting material and being separate from both said sensing and reference electrodes, and being exposed to the ambient atmosphere;

a protonic conductive electrolyte membrane permeable to water vapor, having top and bottom sides, said bottom side of said protonic conductive membrane being in contact with the counter electrode, and the top side of said protonic conductive membrane being in contact with the sensing and reference electrodes;

means, containing a volume of water vapor, for exposing a surface of said counter electrode to said water vapor, the sensing electrode reacting with the gas to produce a change in electrical characteristic between the sensing electrode and the counter electrode; and means for electrical measurement in electrical contact between the sensing electrode and the counter electrode, wherein the electrical conducting material of at least one of said sensing, counter, and reference electrodes is a proton-electron mixed conductive material having 10-50 wt % of a proton conductor material and 50-90 wt % of a first and a second electrical conductor material;

whereby, in a positive ambient concentration of said gas, said electrical measurement means detects changes in said electrical characteristic.

53. The electrochemical gas sensor as defined in claim 52, further comprising:

means for applying a DC power across said protonic electrolyte membrane in electrical contact between the sensing electrode and said counter electrode, whereby the gas is transported away from the counter electrode when the DC power means applies a DC power across said protonic electrolyte membrane.

54. The electrochemical gas sensor as defined in claim 52, wherein said means for exposing a surface of said counter electrode to said water vapor further contains an antifreeze additive.

55. The electrochemical gas sensor as defined in claim 52, wherein the surface of said sensing electrode that is exposed to the ambient atmosphere has a surface area smaller than the surface area of the surface of the counter electrode that is exposed to said water vapor, whereby the first protonic conductive electrolyte membrane is exposed to substantially 100 percent relative humidity, and a positive pressure of said water vapor exists from the surface of said counter electrode that is exposed to said water vapor to the surface of said sensing electrode that is exposed to the ambient atmosphere.

56. The electrochemical gas sensor as defined in claim 55, wherein the surface area of the surface of the counter electrode that is exposed to said water vapor is separated from said means for exposing a surface of said counter electrode to said water vapor by a hydrophobic membrane permeable to water vapor and substantially impervious to water.

57. The electrochemical gas sensor as defined in claim 52, wherein at least one of the surfaces of said protonic conductive electrolyte membrane in contact with one of the sensing, counter, and reference electrodes is substantially nonplanar.

58. The electrochemical gas sensor as defined in claim 52, wherein at least one of the sensing, counter, and reference electrodes is comprised of film having a thickness in the range of about 50 Angstroms to 10,000 Angstroms.

59. The electrochemical gas sensor as defined in claim 58, wherein the film is substantially composed of a noble metal.

60. The electrochemical gas sensor as defined in claim 59, wherein the noble metal is platinum.

61. The electrochemical gas sensor as defined in claim 52, wherein the protonic conductive electrolyte membrane is substantially comprised of a solid, perfluorinated, ion-exchange polymer.

62. The electrochemical gas sensor as defined in claim 52, wherein the protonic conductive electrolyte membrane is a hydrated metal oxide protonic conductor electrolyte membrane.

63. The electrochemical gas sensor as defined in claim 52, wherein the proton conductor material for said at least one of the sensing, counter, and reference electrodes is a copolymer having a tetrafluoroethylene backbone with a side chain of perfluorinated monomers containing at least one of a sulfonic acid group or a carboxylic acid group.

64. The electrochemical gas sensor as defined in claim 52, wherein one of the first and second electrical conductor materials for said at least one of the sensing, counter, and reference electrodes is about 50-99 wt % of carbon black, and the other of the first and second electrical conductor materials for said at least one of the sensing, counter, and reference electrodes is about 1-50 wt % of platinum.

65. The electrochemical gas sensor as defined in claim 52, wherein one of the first and second electrical conductor materials for said at least one of the sensing, counter, and reference electrodes is about 50-99 wt % of carbon black, and the other of the first and second electrical conductor materials for said at least one of the sensing, counter, and reference electrodes is about 1-50 wt % of Ru oxide.

*66. A two-electrode electrochemical gas sensor for quantitative measurement of a gas in an ambient atmosphere comprising:*

*a sensing electrode permeable to water vapor and comprised of an electrical conducting material and having a surface exposed to the ambient atmosphere;*

*a counter electrode permeable to water vapor and comprised of an electrical conducting material;*

*a first protonic conductive electrolyte membrane permeable to water vapor and situated between and in contact with the sensing and counter electrodes, the sensing electrode and the counter electrode being the only two electrodes in contact with the first protonic conductive electrolyte membrane and the sensing electrode reacting with the gas to produce a change in electrical characteristic between the sensing electrode and the counter electrode;*

*means for electrical measurement electrically connected to said sensing and counter electrodes;*

*means, containing a volume of water vapor, for exposing a surface of said counter electrode to said water vapor,*

*wherein the electrical conducting material of at least one of said sensing and counter electrodes is a proton-electron mixed conductive material having 10-50 wt % of a proton conductor material and 50-90 wt % of a first and a second electrical conductor material;*

*whereby, in a positive ambient atmosphere concentration of said gas, said electrical measurement means detects changes in said electrical characteristic.*

*67. An electrochemical gas sensor for quantitative measurement of a gas in an ambient atmosphere comprising:*

*a sensing electrode permeable to water vapor and comprised of an electrical conducting material and having a surface exposed to the ambient atmosphere;*

*a counter electrode permeable to water vapor and comprised of an electrical conducting material;*

*a first protonic conductive electrolyte membrane permeable to water vapor and situated between and in contact with the sensing and counter electrodes, the sensing electrode reacting with the gas to produce a change in electrical characteristic between the sensing electrode and the counter electrode in the absence of an applied voltage to the sensing electrode;*

*means for electrical measurement electrically connected to said sensing and counter electrodes;*

*means, containing a volume of water vapor, for exposing a surface of said counter electrode to said water vapor,*

*wherein the electrical conducting material of at least one of said sensing and counter electrodes is a proton-electron mixed conductive material having 10-50 wt % of a proton conductor material and 50-90 wt % of a first and a second electrical conductor material;*

*whereby, in a positive ambient atmosphere concentration of said gas, said electrical measurement means detects changes in said electrical characteristic.*

*68. A non-biased electrochemical gas sensor for quantitative measurement of a gas in an ambient atmosphere comprising:*

*a sensing electrode permeable to water vapor and comprised of an electrical conducting material and having a surface exposed to the ambient atmosphere;*

*a counter electrode permeable to water vapor and comprised of an electrical conducting material;*

*a first protonic conductive electrolyte membrane permeable to water vapor and situated between and in contact with the sensing and counter electrodes, the sensing electrode reacting with the gas to produce a change in electrical characteristic between the sensing electrode and the counter electrode;*

*means for electrical measurement electrically connected to said sensing and counter electrodes;*

*means, containing a volume of water vapor, for exposing a surface of said counter electrode to said water vapor,*

*wherein the electrical conducting material of at least one of said sensing and counter electrodes is a proton-electron mixed conductive material having 10-50 wt % of a proton conductor material and 50-90 wt % of a first and a second electrical conductor material;*

*whereby, in a positive ambient atmosphere concentration of said gas, said electrical measurement means detects changes in said electrical characteristic in the absence of any biasing voltage.*

*69. The non-biased electrochemical gas sensor of claim 68 in which the sensing electrode and the counter electrode are the only two electrodes in contact with the first protonic conductive electrolyte membrane.*

*70. A two-electrode electrochemical gas sensor for quantitative measurement of a gas in an ambient atmosphere comprising:*

*a sensing electrode permeable to water vapor and comprised of an electrical conducting material and having a surface exposed to the ambient atmosphere;*

*a counter electrode permeable to water vapor and comprised of an electrical conducting material;*

*a first protonic conductive electrolyte membrane permeable to water vapor and situated between and in contact with the sensing and counter electrodes, the sensing electrode and the counter electrode being the only two electrodes in contact with the first protonic conductive electrolyte membrane, and the sensing electrode reacting with the gas to produce a change in electrical characteristic between the sensing electrode and the counter electrode in the absence of an applied voltage to the sensing electrode;*

*means for electrical measurement electrically connected to said sensing and counter electrodes;*

*means, containing a volume of water vapor, for exposing a surface of said counter electrode to said water vapor,*

*wherein the electrical conducting material of at least one of said sensing and counter electrodes is a proton-electron mixed conductive material having 10-50 wt % of a proton conductor material and 50-90 wt % of a first and a second electrical conductor material;*

*whereby, in a positive ambient atmosphere concentration of said gas, said electrical measurement means detects changes in said electrical characteristic.*

*71. An electrochemical gas sensor for quantitative measurement of a gas in an ambient atmosphere comprising:*

*a sensing electrode permeable to water vapor and comprised of an electrical conducting material and having a surface exposed to the ambient atmosphere;*

*a counter electrode permeable to water vapor and comprised of an electrical conducting material;*

*a first protonic conductive electrolyte membrane permeable to water vapor and situated between and in contact with the sensing and counter electrodes, the sensing electrode reacting with the gas to produce a change in electrical characteristic between the sensing electrode and the counter electrode, the sensing electrode and the counter electrode being on opposite sides of the first protonic conductive electrolyte membrane;*

*means for electrical measurement electrically connected to said sensing and counter electrodes;*

*means, containing a volume of water vapor, for exposing a surface of said counter electrode to said water vapor,*

*wherein the electrical conducting material of at least one of said sensing and counter electrodes is a proton-electron mixed conductive material having 10-50 wt % of a proton conductor material and 50-90 wt % of a first and a second electrical conductor material;*

*whereby, in a positive ambient atmosphere concentration of said gas, said electrical measurement means detects changes in said electrical characteristic.*

*72. The electrochemical gas sensor of claim 71 in which the sensing electrode and the counter electrode are the only two electrodes in contact with the first protonic conductive electrolyte membrane.*

*73. The electrochemical gas sensor of claim 72 in which the sensing electrode reacts with the gas to produce a change in electrical characteristic between the sensing electrode and the counter electrode in the absence of an applied voltage to the sensing electrode.*

*74. The electrochemical gas sensor of claim 71 in which the sensing electrode reacts with the gas to produce a change in electrical characteristic between the sensing electrode and the counter electrode in the absence of an applied voltage to the sensing electrode.*

*75. An electrochemical gas sensor for quantitative measurement of a gas in an ambient atmosphere at room temperature comprising:*

*a sensing electrode permeable to water vapor and comprised of an electrical conducting material and having a surface exposed to the ambient atmosphere;*

*a counter electrode permeable to water vapor and comprised of an electrical conducting material;*

*a first protonic conductive electrolyte membrane permeable to water vapor and situated between and in contact with the sensing and counter electrodes, the sensing electrode reacting with the gas to produce a change in electrical characteristic between the sensing electrode and the counter electrode;*

*means for electrical measurement electrically connected to said sensing and counter electrodes, said means for electrical measurement being capable of detecting changes in said electrical characteristic in a positive ambient atmosphere concentration of said gas;*

*means, containing a volume of water vapor, for exposing a surface of said counter electrode to said water vapor,*

*wherein the electrical conducting material of at least one of said sensing and counter electrodes is a proton-electron mixed conductive material having 10-50 wt % of a proton conductor material and 50-90 wt % of a first and a second electrical conductor material.*

*76. The electrochemical gas sensor as defined in claim 75, wherein said water vapor containing means contains a volume of water and an antifreeze additive.*

*77. The electrochemical gas sensor as defined in claim 75, wherein the surface of said sensing electrode that is exposed to the ambient atmosphere has a surface area that is smaller than the surface area of the surface of the counter electrode that is exposed to said water vapor, whereby the first protonic conductive electrolyte membrane is exposed to substantially 100 percent relative humidity, and a positive pressure of said water vapor exists from the surface of said counter electrode exposed to said water vapor to the surface of said sensing electrode exposed to the ambient atmosphere.*

*78. The electrochemical gas sensor as defined in claim 77, wherein the surface area of the surface of the counter electrode that is exposed to said water vapor is separated from said means for exposing a surface of said counter electrode to said water vapor by a hydrophobic membrane permeable to water vapor and substantially impervious to water.*

*79. The electrochemical gas sensor as defined in claim 75, wherein the first protonic conductive electrolyte membrane has opposing surfaces, each of said opposing surfaces being in contact with one of the sensing and counter electrodes, wherein at least one of the opposing surfaces of said first protonic conductive electrolyte membrane in contact with one of the sensing and counter electrodes is substantially nonplanar.*

*80. The electrochemical gas sensor as defined in claim 75, wherein at least one of the sensing and counter electrodes is comprised of film having a thickness in the range of about 50 Angstroms to 10,000 Angstroms.*

*81. The electrochemical gas sensor as defined in claim 80, wherein the film is substantially composed of a noble metal.*

*82. The electrochemical gas sensor as defined in claim 81, wherein the noble metal is platinum.*

*83. The electrochemical gas sensor as defined in claim 75, wherein the first protonic conductive electrolyte membrane is substantially composed of a solid, perfluorinated, ion-exchange polymer.*

*84. The electrochemical gas sensor as defined in claim 75, wherein the first protonic conductive electrolyte membrane is a hydrated metal oxide protonic conductor electrolyte membrane.*

*85. The electrochemical gas sensor as defined in claim 75, wherein the proton conductor material for said at least one of the sensing and counter electrodes is a copolymer having a tetrafluoroethylene backbone with a side chain of perfluorinated monomers containing at least one of a sulfonic acid group or a carboxylic acid group.*

*86. The electrochemical gas sensor as defined in claim 75, wherein one of the first and second electrical conductor materials for said at least one of the sensing and counter electrodes is about 50-99 wt % of carbon black, and the other of the first and second electrical conductor materials for said at least one of the sensing and counter electrodes is about 1-50 wt % of platinum.*

*87. The electrochemical gas sensor as defined in claim 75, wherein one of the first and second electrical conductor materials for said at least one of the sensing and counter electrodes is about 50-99 wt % of carbon black, and the other of the first and second electrical conductor materials for said at least one of the sensing and counter electrodes is about 1-50 wt % of Ru oxide.*

*88. The electrochemical gas sensor as defined in claim 75, wherein the electrochemical gas sensor further comprises:*

*first and second pump electrodes comprised of an electrical conducting material permeable to water vapor, separate from said sensing and counter electrodes, and situated on opposite sides of and in contact with said first protonic conductive electrolyte membrane, said second pump electrode being situated on the same side of said first protonic conductive membrane as the counter electrode and having a surface thereon exposed to the water vapor in said means for exposing a surface of said counter electrode to said water vapor; and means for applying a DC power across the first protonic conductive electrolyte membrane, said first and second pump electrodes having in electrical connection therebetween said means for applying DC power across the first protonic conductive electrolyte membrane;*

*whereby the gas is transported away from the counter electrode when the DC power means applies a DC power to the first and second pump electrodes.*

*89. The electrochemical gas sensor of claim 88, wherein the electrical conducting material of the first and second pump electrodes is substantially composed of carbon.*

*90. The electrochemical gas sensor as defined in claim 88, wherein the electrical conducting material of the first and second pump electrodes is substantially composed of noble metals.*

*91. The electrochemical gas sensor as defined in claim 88, wherein the electrical conducting material of the first and second pump electrodes is substantially composed of conductive hydrated metal oxides.*

*92. The electrochemical gas sensor as defined in claim 88, wherein at least one of the first and second pump electrodes is comprised of a film having a thickness in the range of about 50 Angstroms to 10,000 Angstroms.*

*93. The electrochemical gas sensor as defined in claim 88, wherein the electrical conducting material of said first and second pump electrodes is a proton-electron mixed conductive material having 10-50 wt % of a proton conductor material and 50-90 wt % of a first and a second electrical conductor material.*

*94. The electrochemical gas sensor as defined in claim 93, wherein the proton conductor material for both the first and second pump electrodes is a copolymer having a tetrafluoroethylene backbone with a side chain of perfluorinated monomers containing at least one of a sulfonic acid group or a carboxylic acid group.*

*95. The electrochemical gas sensor as defined in claim 93, wherein one of the first and second electrical conductor materials for the first pump electrode is about 50-99 wt % of carbon black, and the other of the first and second electrical conductor materials for the first pump electrode is 1 to 50 wt % of platinum.*

*96. The electrochemical gas sensor as defined in claim 93, wherein one of the first and second electrical conductor materials for the second pump electrode is about 50-99 wt % of carbon black, and the other of the first and second electrical conductor materials for the second pump electrode is 1 to 50 wt % of Ru oxide.*

*97. The electrochemical gas sensor as defined in claim 75, wherein the electrochemical gas sensor further comprises:*

*a second protonic conductive electrolyte membrane permeable to water vapor;*

*first and second pump electrodes permeable to water vapor and comprised of an electron conductive material, and being separate from said sensing and counter electrodes and situated on opposite sides of and in contact with said second protonic conductive electrolyte membrane, said means for exposing a surface of said counter electrode to said water vapor exposing a surface of said second pump electrode to said water vapor, and said first pump electrode having a surface exposed to the ambient atmosphere; and*

*means for applying a DC power across said second protonic electrolyte membrane, said first and second pump electrodes having in electrical connection therebetween said means for applying DC power across said second protonic electrolyte membrane;*

*whereby the gas is transported away from the counter electrode when the DC power means applies a DC power to the first and second pump electrodes.*

*98. The electrochemical gas sensor as defined in claim 97, wherein the second protonic conductive electrolyte membrane is substantially composed of a solid, perfluorinated, ion-exchange polymer.*

*99. The electrochemical gas sensor as defined in claim 97, wherein the second protonic conductive electrolyte membrane is a hydrated metal oxide protonic conductor electrolyte membrane.*

*100. The electrochemical gas sensor as defined in claim 97, wherein the surface area of the surface of said first pump electrode that is exposed to the ambient atmosphere is smaller than the surface area of the surface of the second pump electrode that is exposed to said water vapor, whereby the second protonic conductive electrolyte membrane is exposed to substantially 100 percent relative humidity, and a positive pressure of said water vapor exists from the surface of said second pump electrode that is exposed to said water vapor to the surface of said first pump electrode that is exposed to the ambient atmosphere.*

*101. The electrochemical gas sensor as defined in claim 100, wherein the surface area of the surface of the second pump electrode that is exposed to said water vapor is separated from said means for exposing a surface of said counter electrode to said water vapor by a hydrophobic membrane permeable to water vapor and substantially impervious to water.*

*102. The electrochemical gas sensor as defined in claim 75, further comprising:*

*means for applying a DC pulse power source across the first protonic conductive membrane, said sensing and counter electrodes having in electrical connection therebetween said means for applying DC pulse power across the first protonic conductive membrane; and*

*switch means for alternating the connection between the sensing and counter electrodes from the electrical measurement means to the DC pulse power means;*

*whereby, in a positive ambient atmosphere concentration of said gas, said electrical measurement means detects changes in said electrical characteristic when said switch means connects said electrical measurement means to the sensing and counter electrodes; and*

*whereby said DC pulse power means moves the gas away from a side of the gas sensor where the counter electrode*

*is placed when said switch means connects said DC pulse power means to the sensing and counter electrodes.*

*103. The electrochemical gas sensor as defined in claim 75, wherein the gas is CO.*

*104. The electrochemical gas sensor as defined in claim 75, wherein the gas is $NO_x$.*

*105. The electrochemical gas sensor as defined in claim 75, wherein the gas is hydrogen.*

*106. The electrochemical gas sensor as defined in claim 75, wherein the gas is $H_2S$.*

*107. The electrochemical gas sensor as defined in claim 75, wherein the gas is $H_2O$ vapor.*

*108. The electrochemical gas sensor as defined in claim 75, wherein the gas is alcohol vapor.*

*109. An electrochemical gas sensor for quantitative measurement of a gas in an ambient atmosphere at room temperature comprising:*

*a sensing electrode permeable to water vapor and comprised of an electrical conducting material and being exposed to the ambient atmosphere;*

*a reference electrode permeable to water vapor and comprised of an electrical conducting material;*

*a counter electrode permeable to water vapor and comprised of an electrical conducting material and being separate from both said sensing and reference electrodes, and being exposed to the ambient atmosphere;*

*a protonic conductive electrolyte membrane permeable to water vapor, having top and bottom sides, said bottom side of said protonic conductive membrane being in contact with the counter electrode, and the top side of said protonic conductive membrane being in contact with the sensing and reference electrodes;*

*means, containing a volume of water vapor, for exposing a surface of said counter electrode to said water vapor, the sensing electrode reacting with the gas to produce a change in electrical characteristic between the sensing electrode and the counter electrode; and*

*means for electrical measurement in electrical contact between the sensing electrode and the counter electrode,*

*wherein the electrical conducting material of at least one of said sensing, counter, and reference electrodes is a proton-electron mixed conductive material having 10-50 wt % of a proton conductor material and 50-90 wt % of a first and a second electrical conductor material;*

*whereby, in a positive ambient concentration of said gas, said electrical measurement means detects changes in said electrical characteristic.*

*110. The electrochemical gas sensor as defined in claim 109, further comprising:*

*means for applying a DC power across said protonic electrolyte membrane in electrical contact between the sensing electrode and said counter electrode, whereby the gas is transported away from the counter electrode when the DC power means applies a DC power across said protonic electrolyte membrane.*

*111. The electrochemical gas sensor as defined in claim 109, wherein said means for exposing a surface of said counter electrode to said water vapor further contains an antifreeze additive.*

*112. The electrochemical gas sensor as defined in claim 109, wherein the surface of said sensing electrode that is exposed to the ambient atmosphere has a surface area smaller than the surface area of the surface of the counter electrode that is exposed to said water vapor, whereby the first protonic conductive electrolyte membrane is exposed to substantially 100 percent relative humidity, and a positive pressure of said water vapor exists from the surface of said counter electrode that is exposed to said water vapor to the surface of said sensing electrode that is exposed to the ambient atmosphere.*

*113. The electrochemical gas sensor as defined in claim 112, wherein the surface area of the surface of the counter electrode that is exposed to said water vapor is separated from said means for exposing a surface of said counter electrode to said water vapor by a hydrophobic membrane permeable to water vapor and substantially impervious to water.*

*114. The electrochemical gas sensor as defined in claim 109, wherein at least one of the surfaces of said protonic conductive electrolyte membrane in contact with one of the sensing, counter, and reference electrodes is substantially nonplanar.*

*115. The electrochemical gas sensor as defined in claim 109, wherein at least one of the sensing, counter, and reference electrodes is comprised of film having a thickness in the range of about 50 Angstroms to 10,000 Angstroms.*

*116. The electrochemical gas sensor as defined in claim 115, wherein the film is substantially composed of a noble metal.*

*117. The electrochemical gas sensor as defined in claim 116, wherein the noble metal is platinum.*

*118. The electrochemical gas sensor as defined in claim 109, wherein the protonic conductive electrolyte membrane is substantially comprised of a solid, perfluorinated, ion-exchange polymer.*

*119. The electrochemical gas sensor as defined in claim 109, wherein the protonic conductive electrolyte membrane is a hydrated metal oxide protonic conductor electrolyte membrane.*

*120. The electrochemical gas sensor as defined in claim 109, wherein the proton conductor material for said at least one of the sensing, counter, and reference electrodes is a copolymer having a tetrafluoroethylene backbone with a side chain of perfluorinated monomers containing at least one of a sulfonic acid group or a carboxylic acid group.*

*121. The electrochemical gas sensor as defined in claim 109, wherein one of the first and second electrical conductor materials for said at least one of the sensing, counter, and reference electrodes is about 50-99 wt % of carbon black, and the other of the first and second electrical conductor materials for said at least one of the sensing, counter, and reference electrodes is about 1-50 wt % of platinum.*

*122. The electrochemical gas sensor as defined in claim 109, wherein one of the first and second electrical conductor materials for said at least one of the sensing, counter, and reference electrodes is about 50-99 wt % of carbon black, and the other of the first and second electrical conductor materials for said at least one of the sensing, counter, and reference electrodes is about 1-50 wt % of Ru oxide.*

*123. A residential electrochemical gas sensor for quantitative measurement of carbon monoxide gas in an ambient atmosphere comprising:*

*a sensing electrode permeable to water vapor and comprised of an electrical conducting material and having a surface exposed to the ambient atmosphere;*

*a counter electrode permeable to water vapor and comprised of an electrical conducting material;*

*a first protonic conductive electrolyte membrane permeable to water vapor and situated between and in contact with the sensing and counter electrodes, the sensing electrode reacting with the carbon monoxide gas to produce a change in electrical characteristic between the sensing electrode and the counter electrode;*

*means for electrical measurement electrically connected to said sensing and counter electrodes;*

*means, containing a volume of water vapor, for exposing a surface of said counter electrode to said water vapor,*

*wherein the electrical conducting material of at least one of said sensing and counter electrodes is a proton-electron mixed conductive material having 10-50 wt % of a proton conductor material and 50-90 wt % of a first and a second electrical conductor material;*

*whereby, in a positive ambient atmosphere concentration of the carbon monoxide gas at room temperature, said electrical measurement means detects changes in said electrical characteristic.*

*124. The electrochemical gas sensor of claim 123 in which the sensing electrode comprises a mixed protonic-electronic conductive electrode.*

*125. A two-electrode residential electrochemical gas sensor for quantitative measurement of carbon monoxide gas in an ambient atmosphere comprising:*

*a sensing electrode permeable to water vapor and comprised of an electrical conducting material and having a surface exposed to the ambient atmosphere;*

*a counter electrode permeable to water vapor and comprised of an electrical conducting material;*

*a first protonic conductive electrolyte membrane permeable to water vapor and situated between and in contact with the sensing and counter electrodes, the sensing electrode and the counter electrode being the only two electrodes in contact with the first protonic conductive electrolyte membrane, and the sensing electrode reacting with the carbon monoxide gas to produce a change in electrical characteristic between the sensing electrode and the counter electrode in the absence of an applied voltage to the sensing electrode;*

*means for electrical measurement electrically connected to said sensing and counter electrodes;*

*means, containing a volume of water vapor, for exposing a surface of said counter electrode to said water vapor,*

*wherein the electrical conducting material of at least one of said sensing and counter electrodes is a proton-electron mixed conductive material having 10-50 wt % of a proton conductor material and 50-90 wt % of a first and a second electrical conductor material;*

*whereby, in a positive ambient atmosphere concentration of the carbon monoxide gas at room temperature, said electrical measurement means detects changes in said electrical characteristic;*

*wherein each of the sensing electrode and the counter electrode comprise a mixed protonic-electronic conductive electrode including platinum, carbon and a copolymer having a tetrafluoroethylene backbone with a side chain of perfluorinated monomers containing a sulfonic acid group; and*

*wherein the protonic conductive solid electrolyte membrane is substantially comprised of a solid, perfluorinated, ion-exchange polymer.*

*126. The two-electrode electrochemical gas sensor as defined in claim 125, wherein the sensing and counter electrodes have a diameter in a range of 1 mm to 15 mm, and the protonic conductive electrolyte membrane has a thickness in a range of 0.1 mm to 1 mm.*

*127. The two-electrode electrochemical gas sensor as defined in claim 125, wherein the sensing and counter electrodes have a diameter of about 15 mm, and the protonic conductive electrolyte membrane has a thickness of about 0.17 mm.*

*128. The two-electrode electrochemical gas sensor as defined in claim 125, wherein the electrical conducting material of at least one of said sensing and counter electrodes is a proton-electron mixed conductive material having at least approximately 25 wt % of a proton conductor material.*

*129. The two-electrode electrochemical gas sensor as defined in claim 125, wherein said counter electrode is exposed to said water vapor at a 100% relative humidity.*

*130. The two-electrode electrochemical gas sensor as defined in claim 125, wherein the surface of said sensing electrode that is exposed to the ambient atmosphere has a surface area that is smaller than the surface area of the surface of the counter electrode that is exposed to said water vapor, whereby a positive pressure of said water vapor exists from the surface of said counter electrode exposed to said water vapor to the surface of said sensing electrode exposed to the ambient atmosphere.*

* * * * *